US012096735B2

(12) United States Patent
Valverde et al.

(10) Patent No.: US 12,096,735 B2
(45) Date of Patent: Sep. 24, 2024

(54) METHOD AND SYSTEM FOR TIME OF POLLINATING CEREAL CROPS

(71) Applicant: Accelerated Ag Technologies, LLC, Ankeny, IA (US)

(72) Inventors: Federico Valverde, Polk City, IA (US); Elizabeth Ann Trecker, Johnston, IA (US); Michael J. Lauer, Des Moines, IA (US); Mark Gee, Johnston, IA (US); George Singletary, Ankeny, IA (US); Todd Krone, Des Moines, IA (US); Jason Cope, Ankeny, IA (US); Chase Kramer, Des Moines, IA (US); Anthony Stefani, Grimes, IA (US)

(73) Assignee: PowerPollen, Inc., Ames, IA (US)

( * ) Notice: Subject to any disclaimer, the term of this patent is extended or adjusted under 35 U.S.C. 154(b) by 560 days.

(21) Appl. No.: 17/005,515

(22) Filed: Aug. 28, 2020

(65) Prior Publication Data

US 2021/0059276 A1 Mar. 4, 2021

Related U.S. Application Data

(60) Provisional application No. 62/894,354, filed on Aug. 30, 2019.

(51) Int. Cl.
*A01H 1/02* (2006.01)
*A23J 1/14* (2006.01)
(Continued)

(52) U.S. Cl.
CPC ............... *A01H 1/02* (2013.01); *A23J 1/148* (2013.01); *A23J 3/14* (2013.01); *A23L 11/31* (2016.08);
(Continued)

(58) Field of Classification Search
CPC .......... A23L 11/33; A23L 11/32; A23L 11/31; A01H 1/02; A23J 3/14; A23J 1/148; A23J 3/346; A23J 1/144
(Continued)

(56) References Cited

U.S. PATENT DOCUMENTS 4,087,937 A 5/1978 Meader
5,596,838 A 1/1997 Greaves et al.
(Continued)

FOREIGN PATENT DOCUMENTS

JP 4177494 11/2008
JP 2009040703 A 2/2009
(Continued)

OTHER PUBLICATIONS

A. Marceau, S. Saint-Jean, B. Loubet, X. Foueillassar, L. Huber, Biophysical characteristics of maize pollen: Variability during emission and consequences on cross-pollination risks, Field Crops Research (2012) 127: pp. 51-63.
(Continued)

*Primary Examiner* — Subbalakshmi Prakash
(74) *Attorney, Agent, or Firm* — Brick Gentry PC; Brian J. Laurenzo; Charles M. Forney

(57) ABSTRACT

A method of identifying a selected pollination window in a Poaceae crop by monitoring one or more environmental parameters and identifying a selected pollination window based upon the monitored parameters. The correct selection of parameters has been shown to markedly increase seed set, yield, and/or other desirable characteristics, including but not limited to preferred content of oil, starch, protein, and/or other nutritional components. Parameters may include one or more of: temperature, relative humidity, and vapor pressure deficit.

14 Claims, 6 Drawing Sheets

(51) Int. Cl.
*A23J 3/14* (2006.01)
*A23J 3/34* (2006.01)
*A23L 11/30* (2016.01)

(52) U.S. Cl.
CPC ............... *A23L 11/32* (2016.08); *A23L 11/33* (2016.08); *A23J 1/144* (2013.01); *A23J 3/346* (2013.01)

(58) Field of Classification Search
USPC .......................................................... 47/1.47
See application file for complete search history.

(56) References Cited

U.S. PATENT DOCUMENTS

| | | | |
|---|---|---|---|
| 5,689,914 | A | 11/1997 | Greaves et al. |
| 5,694,700 | A | 12/1997 | Greaves et al. |
| 6,141,904 | A | 11/2000 | Greaves et al. |
| 6,146,884 | A | 11/2000 | Coonrod et al. |
| 9,433,161 | B2 | 9/2016 | Cope et al. |
| 2013/0118067 | A1 | 5/2013 | Cope et al. |
| 2014/0115730 | A1 | 4/2014 | Cope |
| 2014/0223812 | A1 | 8/2014 | Cope et al. |
| 2014/0271535 | A1 | 9/2014 | Yamashita |
| 2015/0253273 | A1 | 9/2015 | Heidmann et al. |

FOREIGN PATENT DOCUMENTS

| | | |
|---|---|---|
| SU | 1606037 | 11/1990 |
| WO | 2012125593 | 9/2012 |
| WO | 2014209903 | 12/2014 |
| WO | 2016085355 | 6/2016 |
| WO | 2016196616 | 12/2016 |
| WO | 2016210324 | 12/2016 |
| WO | 2018129302 | 7/2018 |

OTHER PUBLICATIONS

C-L Tsai, D. M. Huber, H. L. Warren, C. Y. Tsai, Effects of cross-pollination on dry matter accumulation, nutrient partitioning and grain yield of maize hybrids grown under different levels of N fertility, Journal of the Science of Food and Agriculture (1991) 57(2): pp. 163-174.
R. T. Weiland, Cross-pollination effects on maize (*Zea mays* L.) hybrid yields, Canadian Journal of Plant Science (1992) 72: pp. 27-33.
F. A. Hoekstra and J. Bruinsma, Respiration and Vitality of Binucleate and Trinucleate Pollen, Physiologia Plantarum (2006) 34(3): pp. 221-225.
M. Nepi, G.G. Franchi, and E. Pacini, Pollen hydration status at dispersal: cytophysiological features and strategies, Protoplasma (2001) 216(3-4): pp. 171-180.
M. D. Jones, Time of Day of Pollen Shedding of Some Hay Fever Plants, Journal of Allergy (1952) 23(3): pp. 247-258.
D. B. Walden, Male Gametophyte of *Zea mays* L. I. Some Factors Influencing Fertilization, Crop Science (1967) 7(5): pp. 441-444.
PCT International Search Report dated Nov. 5, 2020, International Application No. PCT/US2020/058337, Filing Date Aug. 28, 2020; Written Opinion of the International Searching Authority for International Application No. PCT/US2020/058337, Filing Date Aug. 28, 2020.
C. Efstathiou, S. Isukapalli, P. Georgopoulos, A mechanistic modeling system for estimating large-scale emissions and transport of pollen and co-allergens, Atmospheric Environment (2011) 45(13): pp. 2260-2276.
B. J. Viner, M. E. Westgate, and R. W. Arritt, A Model to Predict Diurnal Pollen Shed in Maize, Crop Science (2010) 50(1), pp. 235-245.
M. Chamecki, S. C. Gleicher, N. S. Dufault, S. A. Isard, Diurnal variation in settling velocity of pollen released from maize and consequences for atmospheric dispersion and cross-pollination, Agricultural and Forest Meteorology (2011) 151: pp. 1055-1065.
L. A. Tatum and W. R. Kehr, Observations on Factors Affecting Seed-set with Inbred Strains of Dent Corn, Agronomy Journal (1951) 43(6): pp. 270-275.
A.R. Hallauer and J.H. Sears (1966) Influence of Time of Day and Silk Treatment on Seed Set in Maize, Crop Science, 6(2): pp. 216-218.
European Patent Office, Communication pursuant to Article 94(3) EPC, Application No. 20768805.2-1118, Office Action issued Jun. 7, 2023.
China National Intellectual Property Administration, Application No. 2020800699293, Office Action issued Feb. 18, 2023.
Chilean Patent Office, Application No. 202200494, Written Opinion issued Oct. 25, 2023.
Efstathiou, Christos et al—Atmospheric Environment—A mechanistic modeling system for estimating large-scale emissions and transport of pollen and co-allergens—vol. 45, Issue 13, Apr. 2011, pp. 2260-2276.
Chamecki, Marcelo et al—Agricultural and Forest Meteorology, Diurnal variaton in settling velocity of pollen released from maize and consequences for atmospheric dispersion and cross-pollination—vol. 151, Issue 8, Aug. 15, 2011, pp. 1055-1065.
Viner, Brian J.; Westgate, Mark E.; Arritt, Raymond W.—A Model to Predict Diurnal Pollen Shed in Maize—Crop Science vol. 50, Issue 1, p. 235-245.
Office Action dated Jan. 25, 2024 from Canadian Patent Application 3,152,771, "Method and System for Time of Pollinating Cereal Crop", as received from the Canadian Intellectual Property Office.
International Search Report and Written Opinion dated Nov. 5, 2020, Application No. PCT/US2020/048337.
European Patent Office Rule 161-162 communication dated Apr. 29, 2022, Application No. 20768805.2.

METHOD AND SYSTEM FOR TIME OF POLLINATING CEREAL CROPS

CROSS REFERENCE TO RELATED APPLICATIONS

This application claims priority from U.S. Provisional Patent Application No. 62/894,354 filed Aug. 30, 2019 and titled Method and System for Optimizing Pollination Timing in Poaceae Crops. The entire contents of U.S. Provisional Patent Application No. 62/894,354 are hereby incorporated by reference.

FIELD OF THE INVENTION

This invention relates generally to technologies that allow for, and/or enable, improved output by identifying a selected pollination window of time for pollination. More specifically, this invention relates to the identification of a pollination window based on one or more of a range of measurable and/or monitorable parameters, and optionally to additionally using pollen to pollinate plants at the selected time(s), as well as to methods for identifying plants as being ready to receive pollen at said selected time(s), and further to methods of releasing pollen at one or more selected times based on said range of measurable parameters. In some embodiments, the method optionally does not include a step of intentionally releasing pollen. The invention provides a system that will allow measurements to identify the selected pollination window to maximize yield, seed set, and/or other crop characteristics.

BACKGROUND

The current invention has application to the field of pollination and crop production practices, including but not limited to seed, grain, and biomass production practices, across Poaceae (Gramineae) crops, also known as cereal crops. These include but are not limited to, maize (also called corn), wheat, rice, sorghum, barley, oats, and pearl millet.

This invention is applicable to both hybrid production and non-hybrid production. While hybrid production is most often used for seed production, it may also be used for grain and/or biomass production. Non-hybrid production results when a plant is pollinated by pollen having the same genetic background, such as in self-pollination and sib-pollination. Hybrid plants are the result of fertilization occurring from a male pollen source of one genetic background being crossed to the female reproductive organs of a plant with a different genetic background. Hybridity among crop plants generally gives a yield advantage in commercial production and is therefore preferred, if possible, to open or self-pollinated methods of producing many commercial Poaceae crops. Crop yields began to increase markedly with the widespread introduction of hybrids in the 1940s, and crop yields have continued to increase steadily over time to the present day. In addition, large scale processes to produce higher yields of self-pollinated seeds also have significant potential value.

As will be appreciated by one of skill in the art, the practice of the invention disclosed herein will provide different benefits depending upon the nature of the crop. For crops in which hybrid production is commonplace, current methods of producing seed vary by species, but many methods typically involve the following components: (1) Planting female and male parent plants in a production block arranged in close proximity to one another; (2) locating the production block in an isolated location to reduce exposure to other unrelated or unwanted plants of the same species, and (3) imparting some form of male sterility to the female to render the female parent plants male sterile, thus avoiding the potential for self-pollination, which would ultimately contaminate the seed. Some crops have high rates of self-pollination due to pollen being released within the flower prior to the flower opening. Such crops are often bred to experience very high rates of self-pollinated seed. Practice of the invention can increase the seed set for these self-pollinating crops. Some crops do not require long isolation distances to prevent outcrossing due to the nature of the crop and its pollen characteristics. In such cases, the practice of the current invention may not affect any isolation requirement but will still increase the rate of successful cross pollinations with designated male pollen and also decrease self-pollinations. This is made possible by improving the timing of any such pollinations. Accordingly, depending upon the crop being grown, the practice of the invention may totally or partially eliminate the need for, or reduce dependency upon any one, any two or all three of the costly and resource dependent components: planting males in proximity to females, isolation, and male sterility. Nonetheless, in some embodiments, the invention may be practiced utilizing any one, two, or all three of these components without departing from the scope of the invention.

This invention is applicable to grain production practices. For crops in which grain production is commonplace, current methods of producing grain vary slightly by species, but typically involve planting fields of the same seed variety to produce plants whose mature seeds will result in the desired grain. The plants in such fields are typically self-pollinated or pollinated by neighboring plants in the field and, therefore, are not hybrids. There may be some cross pollination from nearby fields of the same or similar species having different genetic backgrounds.

Practice of the invention described herein will result in efficiencies, higher seed output, increased yield, and/or improvement of other desirable characteristics, including but not limited to preferred content of oil, starch, protein, and/or other nutritional components for both hybrid seed crops and self/sib-pollinated Poaceae crops, whether those crops are grown for seed production, grain production, biomass, or other purposes. The invention is applicable across all geographies in which agricultural Poaceae crops are grown.

SUMMARY OF THE INVENTION

Figure 1:
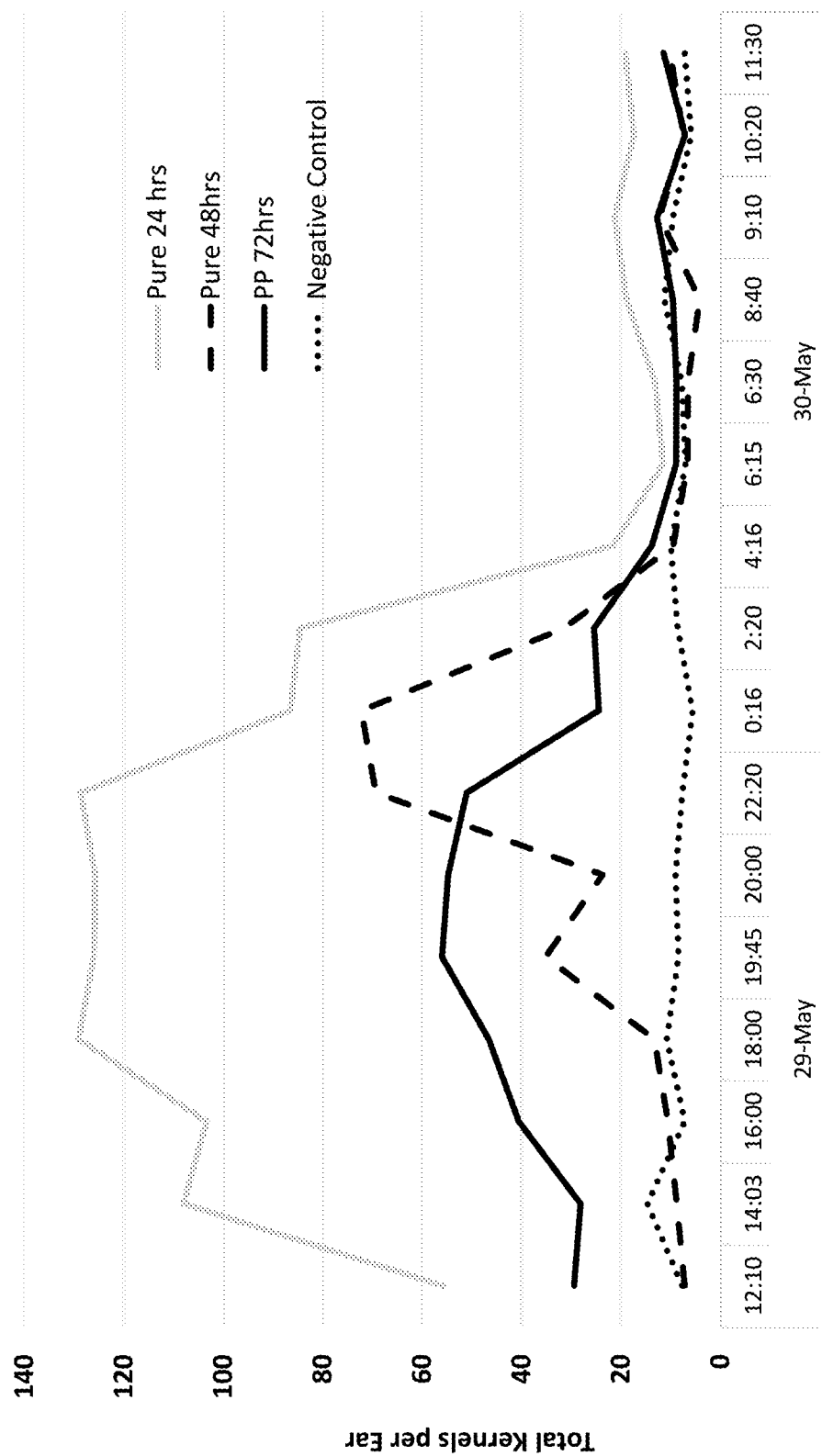
FIG. 1: This figure shows the number of kernels on ears of corn following various treatments with pure preserved pollen and preserved pollen mixed with lactose, over a time course of applications spanning 26 hours.

Provided is a method of identifying a selected pollination window in a Poaceae crop. The method may include monitoring changes in one or more parameters from 12:00 p.m. to 11:59 p.m. on one or more days, wherein said one or more parameters include at least one of temperature, vapor pressure deficit, and relative humidity. The method further includes identifying a selected pollination window which begins when at least one of the following periods of time has been reached: (1) when the temperature has been lower than a previously monitored temperature for at least 30, 45, 60, 75, and/or 90 minutes, (2) when the vapor pressure deficit has been lower than a previously monitored vapor pressure deficit for at least 30, 45, 60, 75, and/or 90 minutes, and/or (3) when the relative humidity has been higher than a previously monitored relative humidity for at least 30, 45, 60, 75, and/or 90 minutes. In some embodiments the selected pollination window may be at least one of the following periods of time: (1) a time between when the temperature has been lower than a previously monitored temperature for at least thirty minutes and 11:59 p.m., (2) a time between when the vapor pressure deficit has been lower than a previously monitored vapor pressure deficit for at least thirty minutes and 11:59 p.m., and (3) a time between when the relative humidity has been higher than a previously monitored relative humidity for at least thirty minutes and 11:59 p.m.

Embodiments of the invention may further include intentionally releasing pollen one or more times during the selected pollination window, such as in proximity to the crop. Pollen may include fresh pollen, preserved pollen, and combinations thereof In the case of preserved pollen, pollen may have been harvested from one or more of a field, a growth chamber, a greenhouse, a glasshouse, a shade house, a hoop house, a vertical farming facility, or a hydroponic facility. Preserved pollen may have been previously collected and preserved by cooling, chilling, cryopreservation, freezing, freeze drying, storage with additives that improve pollen longevity, or storage in liquid nitrogen. Pollen may be from a source with altered circadian rhythm, a source with normal circadian flowering but wherein said male components of a female plant are delayed, a single source, and/or multiple sources. Intentional release of pollen may begin between 12:00 p.m. and 11:59 p.m., such as pollination occurring between 4:00 p.m. and 6:00 p.m.

The selected pollination window may occur when the relative humidity is at least 75%, such as from 75% to 98%. The selected pollination window may occur on a day when at least a portion of the crop is receptive to pollen. Moreover, embodiments of the invention may be practiced on a population of Poaceae plants. The crop may be selected from maize, wheat, rice, sorghum, barley, oats, and pearl millet. Monitoring may occur continuously or at intervals.

In another embodiment of the invention, a method of maximizing at last one desirable characteristic of a Poaceae crop is provided. The method includes intentionally pollinating the crop during a selected pollination window that is between 2 and 6 hours after the maximum recorded temperature of the day, such as between 2.5 to 5.5, 3 to 5, or 3.5 to 4.5 hours after the maximum recorded temperature of the day.

In yet another embodiment of the invention, a method of maximizing at least one desirable characteristic of a Poaceae crop is provided. The method includes intentionally pollinating the crop during a selected pollination window such that the time at halfway through the intentional pollination is between 2 and 6 hours after the maximum recorded temperature of the day, such as between 2.5 to 5.5, 3 to 5, or 3.5 to 4.5 hours after the maximum recorded temperature of the day.

DETAILED DESCRIPTION

The following is a detailed description of an embodiment of technology and methods enabling improved yield, seed set, and other desirable characteristics including but not limited to preferred content of oil, starch, protein, and/or other nutritional components. Such technology and methods may be used for the creation of hybrid seed or grain, or non-hybrid seed or grain from any seed-propagated Poaceae plant species. For ease of discussion and understanding, the following detailed description often refers to the invention for use with maize (also referred to as corn). It should be appreciated that the technology and methods may be used with any seed-propagated Poaceae plants, and corn, or other specifically named plants, are discussed for illustration purposes only and are not intended to be limiting.

In some embodiments, methods of the present invention are applicable to a crop which includes a population of plants, which is defined as 500 or more plants, such as a field of plants, or a population of plants growing in a hydroponic facility, vertical farming facility, or other growing environment. A population of plants may include plants having one, two, three, or more genetically distinct backgrounds. In some embodiments, the methods are applicable to a field of plants. A field may be any size but is typically at least $\frac{1}{10}$ of an acre and may be any size above $\frac{1}{10}$ of an acre. Common field sizes in the United States are between 40 acres and 200 acres. Fields in other areas of the world may be smaller or larger. Accordingly, a field may be, but is not limited to, $\frac{1}{10}$ acre, $\frac{1}{5}$ acre, $\frac{3}{10}$ acre, $\frac{2}{5}$ acre, $\frac{1}{2}$ acre, $\frac{3}{5}$ acre, $\frac{7}{10}$ acre, $\frac{4}{5}$ acre, $\frac{9}{10}$ acre, 1 acre, 2 acres, 3 acres, 4 acres, 5 acres, 6 acres, 7 acres, 8 acres, 9 acres, 10 acres, 11 acres, 12 acres, 13 acres, 14 acres, 15 acres, 16 acres, 17 acres, 18 acres, 19 acres, 20 acres, 25 acres, 30 acres, 35 acres, 40 acres, 45 acres, 50 acres, 55 acres, 60 acres, 65 acres, 70 acres, 75 acres, 80 acres, 85 acres, 90 acres, 95 acres, 100 acres, 105 acres, 110 acres, 115 acres, 120 acres, 125 acres, 130 acres, 135 acres, 140 acres, 145 acres, 150 acres, 155 acres, 160 acres, 165 acres, 170 acres, 175 acres, 180 acres, 185 acres, 190 acres, 195 acres, 200 acres, 205 acres, or 210 acres. An acre may be defined as 4047 square meters. It will be understood by one in the art that the amount of time necessary to intentionally pollinate a field will depend on many factors including, but not limited to, field size, the speed at which pollination may occur, and the number of people and/or devices available to pollinate. In some embodiments, a field of forty acres may take approximately 2.5 hours to intentionally pollinate.

In some conditions, such as a field, the crop is exposed to neighboring plants, which may or may not be biologically compatible to the Poaceae crop to be intentionally pollinated. If biologically compatible and in close enough proximity, the neighboring plants may provide undesirable pollen sources via natural pollination means. In addition, the Poaceae crop to be pollinated may itself provide undesirable pollen sources via natural pollination means. For purposes of this application, "proximity" means that pollen is near enough to the Poaceae crop such that the pollen is capable of pollinating the Poaceae crop. In natural pollination, proximity may mean that plants have been planted and/or grown near to each other. In intentional pollination, proximity may mean that pollen is released and/or applied at such a distance that the pollen is capable of pollinating the Poaceae crop. In some methods of intentional pollination, "proximity" may include, but is not limited to, applying pollen directly to the plant(s) to be pollinated and targeting release toward the plant(s) to be pollinated.

Poaceae plants may be grown for one or more of several purposes, including, but not limited to, seed production, grain production, and biomass production. The ultimate uses of such crops include, but are not limited to, seed to be planted, human food products, animal feed products, fuel sources such as ethanol, biomass, and/or nutritional products. Seed, including hybrid seed, is produced for several purposes. First, seed is produced for various research purposes to evaluate the value of new combinations of genetics. Seed companies devote billions of dollars to research in the pursuit of developing better plant genetics. Seed is also produced for commercial sale to producers, such as farmers, or other consumers. In addition, seed is produced to create the parent seed that is used to grow the parents in a seed production field. This invention can be used to produce any Poaceae hybrid or non-hybrid seed for any purpose. In addition, this invention can be used to maximize yield, seed set, and other desirable characteristics including but not limited to preferred content of oil, starch, protein, and/or other nutritional components in Poaceae crops that are destined to be used as grain, such as seed for use in human food products, animal food products, ethanol production, oil production (such as corn oil), other nutritional products, or any other seed use in which the seed is not intended for planting and in which the seed is typically destroyed or rendered non-viable. Moreover, in some cases, the Poaceae plants may be used for biomass production, including but not limited to hay and silage.

This invention provides an improved method of identifying a selected pollination window for the timing of the intentional release of pollen and, optionally, intentionally applying male pollen to female plants. Identifying a pollination window may include, but is not limited to, selecting a pollination window, choosing a pollination window, detecting a pollination window, and/or recognizing a pollination window. Use of the term "intentional" with regard to pollen application means the specific application of pollen in a way that does not include, or exclusively involve, natural pollination by wind, insect activity or other naturally-occurring conditions. Intentionally applied pollen is pollen that has been applied to a plant as a result of a deliberate human activity, decision, or intervention, and may be applied by hand or by other means. In some embodiments the intentional release of pollen may include releasing pollen in proximity to said crop to be pollinated such that said pollen is capable of pollinating said crop. For the purposes of this invention, the term "preservation" or "preserved pollen" means any storage of collected pollen that results in a level of viability, fertility, or both, which is different than the level of viability, fertility or both, which would occur if the pollen were held in unregulated conditions. This invention may use preserved pollen at any time, including but not limited to when the selected pollination window is outside the period of time during which pollen is normally shedding. The preserved pollen may be pollen that has been frozen, chilled, mixed with other particles or liquids, or otherwise treated to preserve its longevity and viability. Preservation may include conditioning steps immediately upon harvesting the pollen to retain or improve its longevity or viability. Methods used may include, for example, those described in US patent application publications US20170238535 or US20190008144, the entire disclosures of which are hereby incorporated by reference. Preserved pollen may have been preserved by any means that permits the pollen to have the necessary level of viability for the application, including but not limited to various forms of cooling or freezing including, but not limited to, chilling, cryopreservation, freeze drying, storage with selected additives to prolong viability, or storage in liquid nitrogen.

The acquisition of pollen required to make pollinations can be via a pollen bank. A pollen bank is a source of stored pollen that has been collected from one or more pollen sources and stored in such a way that the pollen retains its viability. The plants that have been used as the pollen source for such a pollen bank may have been grown and harvested in any conditions, including but not limited to, a field, a growth chamber, a greenhouse, a glasshouse, a shade house, a hoop house, a vertical farming facility or a hydroponic facility. Pollen from a pollen bank may have been sourced in different ways. For example, in one embodiment, fresh pollen can be harvested from plants grown in a controlled environment in which the circadian rhythm is 2-8 hours ahead of naturally growing female plants in the field. In another embodiment, the pollen which is stored in the bank may be preserved pollen that was collected days, weeks, months or years prior to its eventual removal from the bank for pollinating purposes.

Pollen grains are small and can be very delicate. Their ability to successfully pollinate a female can be compromised by a range of environmental stresses and can also be impacted by inherent qualities passed on by the plant that originally produced the pollen. Pollen performance (i.e. speed of germination, vigor of tube growth, and associated characteristics) can be referred to as pollen vigor, whereas the ability of pollen to successfully sire viable seeds may be referred to as pollen viability (Shivanna, K R et al. (1991) Theor. Appl. Genet. 81(1):38-42). Pollen vigor and viability can vary significantly among plant species, cultivars, and varieties. Ensuring delivery of pollen by suitable means at the selected pollination window of time will allow the pollen the highest rate of success in successfully pollinating the target plant, thereby resulting in the highest rate of seed set.

By intentionally delivering, releasing, and/or applying pollen at the selected pollination window of time and for at least a portion of the duration of a plant's fertility period when the plant is receptive to pollen or when the environmental conditions are favorable to the success of pollination, seed set, yield, and/or other desirable characteristics including but not limited to preferred content of oil, starch, protein, and/or other nutritional components can be enhanced, improved, changed, minimized, and/or maximized over that which would have been obtained by relying on natural pollination. However, one of skill in the art will also recognize that the duration of pollen delivery, release, and/or application may also operate on a continuum to achieve varying levels of seed set appropriate for the circumstances. Pollen delivery may be for the entire duration of a plant's fertility period or a portion of the duration of a plant's fertility period. Pollen delivery may occur one or more times per day and/or one or more times per fertility period. Pollen can be delivered, released, and/or applied in any number of ways, including, but not limited to, manually, manually with a small hand mechanical device for semi-automated dispersal, by field driven machinery containing pollen dispersal machinery, or via fully automated dispersal by a self-propelled and/or human guided apparatus such as a drone that has a pollen dispersal device mounted to it, wherein the pollen dispersal is by automatic means, including, but not limited to, mechanical or pneumatic means.

Use of a drone would be especially novel and practical in this method. In one estimation, 450 grams (1 lb) of pollen is more than sufficient, when directed to the silks, to pollinate 8 hectares (20 acres) of female parent corn. This is calculated as follows: 4 pollen grains/kernel×500 kernels/ear×1 ear/plant×26,000 plants/Fac×20 acres×275 ng/pollen=286 grams of pollen. This would allow small drones, which need not be regulated, to be used in the method, and which can be guided using GPS coordinates to focus the pollen dispersal directly over the female plants. When the selected pollination window has been identified, the drones are released to conduct the pollinations in the target crop population. The drones can be activated manually, or in other embodiments, the drones can be activated by signals received from a weather station or other device at the time that the ideal pollination window has been identified and correlated with the time it will take the drones to pollinate the size of the field and the number of plants in the plant population. The drones may need to be refilled with the pollen when the field is of a sufficient size.

This invention can operate in any Poaceae crop plant to improve output. It can operate in any environment including, but not limited to, ideal or target growing environments, off-season environments, or controlled environments (e.g. shade/glass/green/hoop houses, growth chambers, vertical farming facilities, hydroponic facilities, aeroponic facilities etc.), including (but not limited to) the options discussed herein, in other paragraphs of the present application, such as paragraphs [00015] and [0020]. It can also operate in any geography where plants are grown and pollinated.

As will be appreciated by one of skill in the art, added benefits resulting from the practice of this invention include one or more of increased, enhanced, and/or maximized yield, seed set, purity, and other desirable characteristics including but not limited to preferred content of oil, starch, protein, and/or other nutritional components. The deliberate and intentional application of pollen to the fertile female parent plant will result in increased pollination events in comparison to naturally occurring pollinations. Depending upon the pollen selected for use in practicing the invention, pollination rates may be considerably increased and as a result, yield or seed set will also be significantly higher than would otherwise be achieved. Depending upon the condition of the female parent plants, the choice of pollen used, environmental conditions and other factors, yield increases of significantly more than 10% are expected, including yield increases of more than 100% in some circumstances, compared to the expected yield without practicing the method of the invention. Accordingly, yield increases may be 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%. Furthermore, seed set increases may be 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%. In addition, other desirable characteristics including but not limited to preferred content of oil, starch, protein, and/or other nutritional components may be increased or decreased by 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%.

The invention includes identifying a selected pollination window in a Poaceae crop. One aspect of the invention includes monitoring changes, such as by taking measurements and/or relying upon commercial measurements, of particular environmental parameters that can be monitored. These parameters include, but are not limited to: temperature, relative humidity, vapor pressure deficit, and wind speed. Calculations using this data to indicate the selected pollination window(s) to pollinate may result in yields, seed sets, and other desirable characteristics several times beyond pollinating at times which do not fall into the selected pollination window(s). The invention includes monitoring changes in these parameters over time and allows for identification of trends that indicate a selected pollination window is approaching. Monitoring parameters may include measuring parameters, recording parameters, relying upon commercial measurements, and/or using a device or system to monitor parameters and/or alert a user with respect to a selected pollination window. Monitoring parameters over time may include monitoring parameters over the entire time during which a crop is receptive to pollen (also called the fertility period), during one or more days of the fertility period, and/or during a portion of one or more days during the fertility period. Commercial measurements may include monitoring and/or relying upon measurements provided by a service, including but not limited to Weather Underground, The Weather Channel, and others. Pollination can occur when the selected parameters are present or soon predicted to be present, resulting in gained efficiencies and higher seed output.

Experimentation has shown that in order to improve, enhance, or maximize seed set, grain yield, biomass yield, and/or other desirable characteristics as described herein, intentional pollination should be conducted when environmental parameters fall into one or more of the ranges shown in Table 1, below.

TABLE 1

Parameter Ranges of the Invention

| Parameter | Range | Notes |
| --- | --- | --- |
| Temperature | 45-100° F. 7-38° C. | Pollination success improves after temperatures decrease by several degrees from the peak temperature of the day. |
| Relative Humidity | 75-98% | Pollination success improves after relative humidity begins to increase, which is typically tied to a decrease in temperature |
| Wind Speed | 0-20 mph 0-32.2 kph | High wind speeds are incompatible with intentional pollinations because the pollen is easily blown off target |
| Vapour Pressure Deficit (VPD) | 0.1 to 1.5 kPa | Elevated VPD results in increased pollen desiccation. Pollination success improves when VPD starts to decrease. |

In addition, the practice of the invention includes consideration of precipitation levels and air flow conditions. The intentional application of pollen during heavy rainfall, for example, should be avoided because the rain tends to wash pollen off the flower surfaces, negatively impacting pollination success. Likewise, the application of pollen during periods of intense wind should be avoided because the pollen will be less likely to reach its intended target. Furthermore, the intentional application of pollen during times of mist or fog conditions typically have an adverse effect on pollination due to surface condensation. Conditions at RH above 98% are more likely to cause surface condensation.

Embodiments of the present invention include methods of identifying a selected pollination window in a Poaceae crop, methods of maximizing at least one desirable characteristic of a Poaceae crop, and methods of identifying a Poaceae crop as being ready for intentional pollination during a selected pollination window. A selected pollination window may be identified based on one or more parameters, such as environmental parameters where the plant is being grown. A selected pollination window may be dependent on the maximum temperature and/or the maximum vapor pressure deficit and/or the relative humidity on a given day where the plant is located. Most days, and particularly days during the fertility period of the growing season of Poaceae crops, follow a predictable curve of measurements for temperature over a twenty-four-hour day, for example when lasting from midnight (12:00 a.m.). to 11:59 p.m. of the same day. Minimum temperatures are typically reached around dawn on each day. Temperatures then increase after sunrise until a maximum is reached. Typically, the maximum temperature is reached between noon (12:00 p.m.). and 11:59 p.m. of the same day, and is most often in the afternoon. After the maximum is reached, temperature typically decreases for the remainder of the day through the next day's dawn. Accordingly, maximum temperature is often reached in the afternoon, such as the mid-afternoon. Moreover, typically once the temperature begins to decrease after a mid-afternoon maximum, it will continue to decrease. Atypical weather patterns and systems may alter this pattern, but it is uncommon.

Relative humidity oftentimes also follows a predictable pattern during the growing season over a twenty-four-hour day, for example when lasting from midnight (12:00 a.m.). to 11:59 p.m. of the same day. However, this pattern is more heavily influenced by weather patterns and systems than temperature. Nonetheless, during most days of the growing season, maximum relative humidity occurs around the time of the lowest temperature, which is near dawn. This can often be observed by seeing dew early in the morning. As the day progresses, relative humidity decreases. Around the time of maximum temperature, relative humidity is at its minimum. Relative humidity then increases throughout the remainder of the day and through the early morning hours of the following day. Relative humidity directly influences the water relations of a plant and indirectly affects leaf growth, photosynthesis, pollination, occurrence of diseases, and, consequently, economic yield. The dryness of the atmosphere as represented by saturation deficit (100-relative humidity) reduces dry matter production through stomatal control and leaf water potential.

Vapor pressure deficit (sometimes VPD) is the difference between the amount of moisture in the air and the amount of moisture the air can hold when it is saturated. VPD oftentimes also follows a predictable pattern during the growing season over a twenty-four-hour day, for example when lasting from midnight (12:00 a.m.). to 11:59 p.m. of the same day. However, this pattern is more heavily influenced by weather patterns and systems than temperature. Nonetheless, during most days of the growing season, minimum VPD occurs around the time of the lowest temperature, which is near dawn. This can often be observed by seeing dew early in the morning. As the day progresses, VPD increases. Around the time of maximum temperature, VPD is also at its maximum. VPD then decreases throughout the remainder of the day and through the early morning hours of the following day. The point of complete saturation is the dew point. Most plants grow well at a VPD of between 0.4 and 1.6 kPa. When the VPD is high, the air is relatively dry, and plant transpiration (water evaporating from plant leaves) is high. As the VPD decreases, transpiration also decreases, or may cease entirely. VPD is a calculated value. To calculate VPD, the saturation vapor pressure (SVP) must be determined. The SVP is the maximum amount of water vapor that the air can hold at a given temperature. As the air temperature increases, the SVP also increases. The actual amount of water vapor in the air at any given moment is the actual vapor pressure (AVP). The relative humidity (RH %) is calculated by the following equation:

$$\left(\frac{AVP}{SVP}\right) \times 100 = RH\ \%$$

The VPD is the SVP minus the AVP.

Accordingly, a step of the method may include monitoring one or more environmental parameters. Environmental parameters may include, but are not limited to, one or more of temperature, vapor pressure deficit, and relative humidity. In some embodiments, monitoring parameters may include measuring parameters, recording measurements of parameters, using measurements provided by a commercial services, and/or using a device or system, such as a computerized device or system, that has been programmed to monitor environmental parameters. In some embodiments, monitoring may take place over an entire fertility period of a Poaceae plant. In some embodiments, monitoring may take place over one or more days or one or more portions of days. In corn, for example, pollen receptivity occurs for around one week. Accordingly, monitoring may occur for one, two, three, four, five, six, seven, eight, nine, or ten days or portions of days, which are typically consecutive but may not be consecutive, such as for example, if on one or more days adverse conditions, including but not limited to rain, make pollination undesirable throughout an entire day. In preferred embodiments, monitoring of parameters may occur from about noon (12:00 p.m.) to about 11:59 p.m. of the same day, on one or more days, such as one or more days when said Poaceae crop is receptive to pollen. Monitoring said parameters may occur manually, automatically, or semi-automatically. Monitoring may occur continuously or in intervals. Intervals may include, but are not limited to a time period of, or at least, every 1 second, 5 seconds, 10 seconds, 15 seconds, 20 seconds, 25 seconds, 30 seconds, 35 seconds, 40 seconds, 45 seconds, 50 seconds, 55 seconds, 60 seconds, 75 seconds, 90 seconds, 105 seconds, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 20 minutes, 25 minutes, 30 minutes, 45 minutes, or 60 minutes.

In one example of embodiments of the invention, a weather station may be used to monitor parameters. The weather station may collect data related to the parameters, including but not limited to temperature and/or relative humidity (moisture in the air). The data from the weather station may optionally be uploaded into a program for calculating further parameters and/or the selected pollination window. In some embodiments vapor pressure deficit may be calculated by the weather station, the program for calculating further parameters, or other means based on temperature and relative humidity measurements by the weather station and/or other probes. In some embodiments monitoring may take place directly at the location of the Poaceae crop to be pollinated, while in other embodiments, monitoring may take place near to said plants. For example, in some embodiments, data collected from a commercial weather station or service near to the Poaceae crop to be pollinated will be sufficient to identify the selected pollination window. Both temperature and relative humidity are preferably the air or atmospheric temperature and air or atmospheric relative humidity, respectively. In some embodiments, monitoring occurs at five-minute intervals.

In some embodiments the selected pollination window begins when at least one of the following periods of time has been reached: (1) when the temperature has been lower than a previously monitored temperature for at least thirty minutes, and/or (2) when the vapor pressure deficit has been lower than a previously monitored vapor pressure deficit for at least thirty minutes, and/or (3) when the relative humidity has been higher than a previously monitored relative humidity for at least thirty minutes. Additionally, or alternatively, in some embodiments the selected pollination window ends when at least one of the following periods of time has been reached: (1) when about 8 hours, about 7 hours, about 6 hours, about 5 hours, about 4 hours, about 3 hours, about 2 hours, about 1 hour, or about 30 minutes has elapsed since the time point of the previously monitored temperature that was taken for the purposes of calculating when the selected pollination window begins, and/or (2) when about 8 hours, about 7 hours, about 6 hours, about 5 hours, about 4 hours, about 3 hours, about 2 hours, about 1 hour, or about 30 minutes has elapsed since the time point of the previously monitored vapor pressure deficit that was taken for the purposes of calculating when the selected pollination window begins, and/or (3) when about 8 hours, about 7 hours, about 6 hours, about 5 hours, about 4 hours, about 3 hours, about 2 hours, about 1 hour, or about 30 minutes has elapsed since the time point of the previously mentioned relative humidity that was taken for the purposes of calculating when the selected pollination window begins and/or (4) when the dew point is reached. The term "about" as used in the forgoing context can, for example, include ±30 minutes, 20 minutes, 10 minutes, 5 minutes, or less than 5 minutes, of the stated time period. Said previously monitored temperature is a temperature determined during the period of same day, for example, wherein the day starts at about midnight (12:00 a.m.) and continues until about 11.59 p.m. of the same day (i.e. within the same 24 hour period) or during the period of the preceding day, for example, when the day starts at about midnight (12:00 a.m.) and continues until about 11:59 p.m. of the same day; and optionally it is a temperature determined during a period between about noon (12:00 p.m.) and about 11.59 p.m. of the same day; and/or preferably it is a temperature determined to be a maximum temperature during said period. Likewise, said previously monitored vapor pressure deficit is a vapor pressure deficit determined during the period of the same day, for example, wherein the day starts at about midnight (12:00 a.m.) and continues until about 11.59 p.m. of the same day (i.e. within the same 24 hour period) or during the period of the preceding day, for example, when the day starts at about midnight (12:00 a.m.) and continues until about 11:59 p.m. of the same day; and optionally it is a vapor pressure deficit determined during a period between about noon (12:00 p.m.) and about 11.59 p.m. of the same day, and preferably it is a vapor pressure deficit determined to be a maximum vapor pressure deficit during said period. Likewise, said previously monitored relative humidity is a relative humidity determined during the period of the same day, for example, wherein the day starts at about midnight (12:00 a.m.) and continues until about 11.59 p.m. of the same day (i.e. within the same 24 hour period) or during the period of the preceding day, for example, when the day starts at about midnight (12:00 a.m.) and continues until about 11:59 p.m. of the same day; and optionally it is a relative humidity determined during a period between about noon (12:00 p.m.) and about 11.59 p.m. of the same day, and preferably it is a relative humidity determined to be a minimum relative humidity during said period. During the selected pollination window, pollen may be intentionally delivered, released, and/or applied, such as in proximity to the crop. When the pollen is intentionally delivered, released, and/or applied in proximity to the crop, the pollen is capable of pollinating the crop. Intentional release of pollen may include the intentional application of pollen as described herein. Based on historical data, pollination may sometimes occur between 4:00 p.m. and 6:00 p.m. when relying on one or more of the described selected pollination windows.

In some embodiments, the selected pollination window may begin when the temperature has been lower than a previously monitored temperature for 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 90 minutes, 105 minutes, 120 minutes, 135 minutes, 150 minutes, 165 minutes, 180 minutes, 195 minutes, 210 minutes, 225 minutes, 240 minutes, 255 minutes, 270 minutes, 285 minutes, or 300 minutes. Additionally, or alternatively, in some embodiments, the selected pollination window may begin when the vapor pressure deficit has been lower than a previously monitored vapor pressure deficit for 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 90 minutes, 105 minutes, 120 minutes, 135 minutes, 150 minutes, 165 minutes, 180 minutes, 195 minutes, 210 minutes, 225 minutes, 240 minutes, 255 minutes, 270 minutes, 285 minutes, or 300 minutes. Additionally, or alternatively, in some embodiments, the selected pollination window may begin when the relative humidity has been higher than a previously monitored relative humidity for 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 90 minutes, 105 minutes, 120 minutes, 135 minutes, 150 minutes, 165 minutes, 180 minutes, 195 minutes, 210 minutes, 225 minutes, 240 minutes, 255 minutes, 270 minutes, 285 minutes, or 300 minutes. Additionally, or alternatively, in some embodiments, the selected pollination window may end after 10 minutes, 20 minutes, 30 minutes, 40 minutes, 50 minutes, 60 minutes, 70 minutes, 80 minutes, 90 minutes, 100 minutes, 110 minutes, 120 minutes, 130 minutes, 140 minutes, 150 minutes, 160 minutes, 170 minutes, 180 minutes, 190 minutes, 200 minutes, 210 minutes, 220 minutes, 230 minutes, 240 minutes, 250 minutes, 260 minutes, 270 minutes, 280 minutes, 290 minutes, 300 minutes, 310 minutes, 320 minutes, 330 minutes, 340 minutes, 350 minutes, 360 minutes, 370 minutes, 380 minutes, 390 minutes, 400 minutes.

Methods of the present invention may include enhancing or maximizing at least one desirable characteristic of a Poaceae crop, including but not limited to, yield and seed set, as well as the content of starch, oil, protein, and/or other nutritional components. Such methods may include selecting a pollination window for intentional pollination of the crop, and/or intentionally pollinating the crop during the selected pollination window, wherein the selected pollination window is between 2 hours and 6 hours after the maximum temperature of the day. Said methods of the present invention may also relate to a method of identifying a Poaceae crop as being ready for intentional pollination, by identifying said crop during the selected pollination window based on the above-noted assessment of the timing of the maximum temperature of the day. In some embodiments, the selected pollination window may be selected from the group consisting of (1) 2.5 to 5.5 hours after the maximum recorded temperature of the day, (2) 3 to 5hours after the maximum recorded temperature of the day, and/or (3) 3.5 to 4.5 hours after the maximum recorded temperature of the day. Additionally, or alternatively, in some embodiments, the method may include intentionally pollinating the crop such that the time at halfway through said intentional pollination is between 2 hours and 6 hours after the maximum temperature of the day. In some embodiments, the time at halfway through said intentional pollination is (1) 2.5 to 5.5 hours after the maximum recorded temperature of the day, (2) 3 to 5 hours after the maximum recorded temperature of the day, and/or (3) 3.5 to 4.5 hours after the maximum recorded temperature of the day. In other embodiments, intentional pollination may be 5% complete, 10% complete, 15% complete, 20% complete, 25% complete, 30% complete, 35% complete, 40% complete, 45% complete, 55% complete, 60% complete, 65% complete, 70% complete, 75% complete, 80% complete, 85% complete, 90% complete, 95% complete, or 100% complete at such times. As the skilled person will appreciate, the time required for intentional pollination can vary dependent on the nature of the intentional pollination, the number of Poaceae crop plants to be intentionally pollinated, and/or the area over which the Poaceae crop plants to be intentionally pollinated are presented. However, and without limitation, the time required for intentional pollination can vary from, for example, about 10 minutes to about 8 hours, for example, greater than about 15 minutes, about 20 minutes, about 25 minutes, about 30 minutes, about 45 minutes, about 60 minutes, about 90 minutes, about 120 minutes, about 150 minutes, about 180 minutes, about 210 minutes, about 240 minutes, about 270 minutes, about 300 minutes, about 330 minutes, about 360 minutes, about 390 minutes, about 420 minutes, about 450 minutes, about 480 minutes or more than about 480 minutes.

Methods of the present invention may include maximizing at least one desirable characteristic of a Poaceae crop, including but not limited to, yield and seed set. Such methods may include selecting a pollination window for intentional pollination of the crop, and/or intentionally pollinating the crop during the selected pollination window, wherein the selected pollination window that is between 2 hours and 6 hours after the maximum vapor pressure deficit of the day. Said methods of the present invention may also relate to a method of identifying a Poaceae crop as being ready for intentional pollination, by identifying said crop during the selected pollination window based on the above-noted assessment of the timing of the maximum vapor pressure deficit of the day. In some embodiments, the selected pollination window may be selected from the group consisting of (1) 2.5 to 5.5 hours after the maximum recorded vapor pressure deficit of the day, (2) 3 to 5hours after the maximum recorded vapor pressure deficit of the day, and/or (3) 3.5 to 4.5 hours after the maximum recorded vapor pressure deficit of the day. Moreover, in some embodiments, the method may include intentionally pollinating the crop such that the time at halfway through said intentional pollination is between 2 hours and 6 hours after the maximum vapor pressure deficit of the day. In some embodiments, the time at halfway through said intentional pollination is (1) 2.5 to 5.5 hours after the maximum recorded vapor pressure deficit of the day, (2) 3 to 5 hours after the maximum recorded vapor pressure deficit of the day, and/or (3) 3.5 to 4.5 hours after the maximum recorded vapor pressure deficit of the day. In other embodiments, intentional pollination may be 5% complete, 10% complete, 15% complete, 20% complete, 25% complete, 30% complete, 35% complete, 40% complete, 45% complete, 55% complete, 60% complete, 65% complete, 70% complete, 75% complete, 80% complete, 85% complete, 90% complete, 95% complete, or 100% complete at such times. We refer to the discussion of the time required for intentional pollination, in the preceding paragraph.

Methods of the present invention may include maximizing at least one desirable characteristic of a Poaceae crop, including but not limited to, yield and seed set. Such methods may include selecting a pollination window for intentional pollination of the crop, and/or intentionally pollinating the crop during the selected pollination window, wherein the selected pollination window that is between 2 hours and 6 hours after the minimum relative humidity of the day. Said methods of the present invention may also relate to a method of identifying a Poaceae crop as being ready for intentional pollination, by identifying said crop during the selected pollination window based on the above-noted assessment of the timing of the minimum relative humidity of the day. In some embodiments, the selected pollination window may be selected from the group consisting of (1) 2.5 to 5.5 hours after the minimum recorded relative humidity of the day, (2) 3 to 5 hours after the minimum recorded relative humidity of the day, and/or (3) 3.5 to 4.5 hours after the minimum recorded relative humidity of the day. Moreover, in some embodiments, the method may include intentionally pollinating the crop such that the time at halfway through said intentional pollination is between 2 hours and 6 hours after the minimum recorded relative humidity of the day. In some embodiments, the time at halfway through said intentional pollination is (1) 2.5 to 5.5 hours after the minimum recorded relative humidity of the day, (2) 3 to 5 hours after the minimum recorded relative humidity of the day, and/or (3) 3.5 to 4.5 hours after the minimum recorded relative humidity of the day. In other embodiments, intentional pollination may be 5% complete, 10% complete, 15% complete, 20% complete, 25% complete, 30% complete, 35% complete, 40% complete, 45% complete, 55% complete, 60% complete, 65% complete, 70% complete, 75% complete, 80% complete, 85% complete, 90% complete, 95% complete, or 100% complete at such times. We refer to the discussion of the time required for intentional pollination above.

In accordance with one embodiment of the present invention, a previous reading of a monitored parameter, such as the temperature and/or vapor pressure deficit, can be determined to be a daily maximum for said reading of the parameter, if: (i) it is determined during the period between about noon (12:00 p.m.) and about 11.59 p.m. of the same day, and more typically between about noon and 6:00 pm; (ii) if subsequent multiple consecutive readings of the monitored parameter, such as multiple consecutive subsequent monitored readings of temperature and/or vapor pressure deficit, that follows the previous reading of the monitored parameter, such as the previous reading of the temperature and/or vapor pressure deficit, remains below that previous reading of the monitored parameter for a period of at least 30 minutes, 35 minutes, 40 minutes, 45 minutes, 50 minutes, 55 minutes, 60 minutes, 65 minutes, 70 minutes, 75 minutes, 90 minutes, 105 minutes, 120 minutes, 135 minutes, 150 minutes, 165 minutes, 180 minutes, 195 minutes, 210 minutes, 225 minutes, 240 minutes, 255 minutes, 270 minutes, 285 minutes, or 300 minutes, when determined based on the directly measured parameter at substantially all time points at which the parameter is measured during said period and/or based on a rolling average of the directly measured parameter at all time points during said period; and/or (iii) if subsequent multiple consecutive readings of the monitored parameter, such as multiple consecutive subsequent monitored readings of the temperature and/or vapor pressure deficit, that follows the previously monitored parameter, such as the previous reading of the temperature and/or vapor pressure deficit, falls continually for a period of at least 30 minutes, 35 minutes, 40 minutes, 45 minutes, 50 minutes, 55 minutes, 60 minutes, 65 minutes, 70 minutes, 75 minutes, 90 minutes, 105 minutes, 120 minutes, 135 minutes, 150 minutes, 165 minutes, 180 minutes, 195 minutes, 210 minutes, 225 minutes, 240 minutes, 255 minutes, 270 minutes, 285 minutes, or 300 minutes, when determined based on the directly measured parameter at substantially all time points at which the parameter is measured during said period and/or based on a rolling average of the directly measured parameter at all time points during said period. By "when determined based on the directly measured parameter substantially all time points at which the parameter is measured during said period", as used in the context of options (ii) and (iii) of the preceding paragraph, we include the meaning that this applies to at least 80%, 85%, 90%, 95%, 96%, 97%, 98%, 99% or substantially 100% of the direct measurements of the parameter within the defined time period. The rolling average of a parameter, such as temperature and/or vapor pressure deficit, is an unweighted mean of multiple instances ("n") of the most recently determined consecutive measurements of the parameter at any given time point, which can be calculated by means that are conventional in the art. For example, the calculation of the rolling average of a parameter may involve the calculation of a rolling average of multiple consecutive readings (e.g. wherein n is an integer selected from 2, 3, 4, 5, 6, 7, 8, 9, 10 or more readings) of said parameter, wherein said multiple readings are taken at spaced apart time points over a period of time, and wherein said period of time may be, for example, about 1 minute, about 2 minutes, about 3 minutes, about 4 minutes, about 5 minutes, about 6 minutes, about 7 minutes, about 8 minutes, about 9 minutes, about 10 minutes, about 15 minutes, about 20 minutes, about 25 minutes, about 30 minutes, about 45 minutes, about 60 minutes, about 75 minutes, about 90 minutes or more.

In accordance with one embodiment of the present invention, a previous reading of a monitored parameter, such as the relative humidity, can be determined to be a daily minimum for said reading of the parameter, if: (i) it is determined during the period between about noon (12:00 p.m.) and about 11.59 p.m. of the same day, and more typically between about noon and 6:00 pm; (ii) if subsequent multiple consecutive readings of the monitored parameter, such as multiple consecutive subsequent monitored readings of temperature and/or vapor pressure deficit, that follows the previous reading of the monitored parameter, such as the previous reading of the temperature and/or vapor pressure deficit, remains above that previous reading of the monitored parameter for a period of at least 30 minutes, 35 minutes, 40 minutes, 45 minutes, 50 minutes, 55 minutes, 60 minutes, 65 minutes, 70 minutes, 75 minutes, 90 minutes, 105 minutes, 120 minutes, 135 minutes, 150 minutes, 165 minutes, 180 minutes, 195 minutes, 210 minutes, 225 minutes, 240 minutes, 255 minutes, 270 minutes, 285 minutes, or 300 minutes, when determined based on the directly measured parameter at substantially all time points at which the parameter is measured during said period and/or based on a rolling average of the directly measured parameter at all time points during said period; and/or (iii) if subsequent multiple consecutive readings of the monitored parameter, such as multiple consecutive subsequent monitored readings of the temperature and/or vapor pressure deficit, that follows the previously monitored parameter, such as the previous reading of the temperature and/or vapor pressure deficit, increases continually for a period of at least 30 minutes, 35 minutes, 40 minutes, 45 minutes, 50 minutes, 55 minutes, 60 minutes, 65 minutes, 70 minutes, 75 minutes, 90 minutes, 105 minutes, 120 minutes, 135 minutes, 150 minutes, 165 minutes, 180 minutes, 195 minutes, 210 minutes, 225 minutes, 240 minutes, 255 minutes, 270 minutes, 285 minutes, or 300 minutes, when determined based on the directly measured parameter at substantially all time points at which the parameter is measured during said period and/or based on a rolling average of the directly measured parameter at all time points during said period. By "when determined based on the directly measured parameter substantially all time points at which the parameter is measured during said period", as used in the context of options (ii) and (iii) of the preceding paragraph, we include the meaning that this applies to at least 80%, 85%, 90%, 95%, 96%, 97%, 98%, 99% or substantially 100% of the direct measurements of the parameter within the defined time period. The rolling average of a parameter, such as temperature and/or vapor pressure deficit, is an unweighted mean of multiple instances ("n") of the most recently determined consecutive measurements of the parameter at any given time point, which can be calculated by means that are conventional in the art. For example, the calculation of the rolling average of a parameter may involve the calculation of a rolling average of multiple consecutive readings (e.g. wherein n is an integer selected from 2, 3, 4, 5, 6, 7, 8, 9, 10 or more readings) of said parameter, wherein said multiple readings are taken at spaced apart time points over a period of time, and wherein said period of time may be, for example, about 1 minute, about 2 minutes, about 3 minutes, about 4 minutes, about 5 minutes, about 6 minutes, about 7 minutes, about 8 minutes, about 9 minutes, about 10 minutes, about 15 minutes, about 20 minutes, about 25 minutes, about 30 minutes, about 45 minutes, about 60 minutes, about 75 minutes, about 90 minutes or more.

According to any aspect of the disclosure of the present application wherein the method is a method of selecting a pollination window for intentional pollination of the crop, and/or is a method of identifying a Poaceae crop as being ready for intentional pollination, then optionally the method may be an automated or computer implemented method and/or any one more steps of the method may be an automated and/or computer implemented step.

According to a further aspect of the disclosure, there is provided a data processing unit configured to perform any method described herein as a computer-implementable method. The data processing unit may comprise one or more processors and memory, the memory comprising computer program code configure to cause the processor to perform any method described herein.

According to a further aspect of the disclosure there is provided a computer readable storage medium comprising computer program code configured to cause a processor to perform any computer-implementable method described herein. The computer readable storage medium may be a non-transitory computer readable storage medium.

There may be provided a computer program, which when run on a computer, causes the computer to configure any apparatus, including a circuit, unit, controller, device or system disclosed herein to perform any method disclosed herein. The computer program may be a software implementation. The computer may comprise appropriate hardware, including one or more processors and memory that are configured to perform the method defined by the computer program.

The computer program may be provided on a computer readable medium, which may be a physical computer readable medium such as a disc or a memory device, or may be embodied as a transient signal. Such a transient signal may be a network download, including an internet download. The computer readable medium may be a computer readable storage medium or non-transitory computer readable medium.

The ability to conduct large scale pollinations during the selected pollination window provides a new and inventive technology for agriculture. With receptivity of the female plant parts possible at any time of the day or night, making pollinations with preserved pollen provides great flexibility according to when actual pollinations are made. By nature, fresh and preserved pollen are sensitive to natural conditions, so not all environmental conditions are optimal for the application of pollen. In addition, some parts of the flower, such as the pistil, the stigma, the style, or the ovary, are also sensitive to natural environmental conditions. In some plant species, such as corn, other specialized plant parts, such as the plant silks, are sensitive to natural environmental conditions. According to the present invention, intentional pollination may be during a window of time when the health and viability of flower parts and plant parts is increased. This invention provides a tool for knowing when to pollinate to achieve the maximum desired characteristics.

Using data from across multiple experiments, it has been shown that pollinating at the selected pollination window of time as determined in accordance with the present invention can result in three-fold more kernels than average, and ten-fold more kernels than pollinating at other times. Moreover, results related to seed set and yield are not significantly impacted by the age of the pollen used (provided it has been stored appropriately to retain necessary levels of viability), nor by the wind speed.

The invention can be used by growers to increase seed set, grain yield, or biomass yield above the seed set or yield that can be obtained using current commercial practices. In a typical field, pollen sheds at varying intensities, with specific periods during which pollen is heavily shed, and other periods during which there may be no pollen, or almost no pollen being shed. In typical fields, the male plants are planted close enough to the female plants that some of the male plants' pollen will reach the female plants by natural means, primarily by wind and insects. The potential for this pollen to fertilize the female plants depends on the time of day the pollen reaches the female plant and the condition of the female plant at the time of pollen landing on the target areas. For example, pollen is often naturally released in large quantities at times such that even if it successfully lands on the female, successful fertilization is unlikely due to temperature, relative humidity, and/or vapor pressure conditions and the negative impact those conditions have on the likelihood of fertilization being successful. These environmental conditions may be occurring during the time of heaviest pollen shed, which has long been assumed to be the time during which the most successful pollinations occur. For example, data collected by the Applicant from commercial corn fields in the Midwest US indicated a dramatic variation in percent seed set, ranging from 22% seed set to 78% seed set, using the most accepted conventional, commercial practices currently available. Lack of sufficient pollen at the appropriate time is the primary factor limiting kernel set. Poor environmental conditions contribute to this problem.

In contrast, by taking advantage of the selected window of time for intentional pollination, growers can avoid relying on the natural periods of heavy pollen shed, and instead rely on intentionally pollinating at the times when the environmental conditions are most supportive of successful pollination. Accordingly, sufficient pollen is available at the appropriate time. This will result in a significant increase in seed set or grain/biomass yield. This invention thereby overcomes the challenges posed by lack of sufficient pollen at the appropriate time. Applicants' data has demonstrated that by practicing the invention as outlined herein, seeds per ear and saleable seed units increased from up to 32% relative to the untreated plants, directly reflecting an increase in seed set.

The following examples illustrate the present invention in more detail and are illustrative of how the invention described herein could be implemented in corn. The basic method could apply to any Poaceae crop with crop specific modifications as appropriate.

EXAMPLE 1

A study using maize was conducted in May, 2019 at a farm located in Texas, USA. Previous studies conducted by the inventors have indicated that greater fertilization success can be achieved at time points outside of the times at which plants naturally release pollen, in which fertilization only occurs during a window of time in the morning hours. This experiment was designed to test the productivity of pollinations made over a 24-hour period while simultaneously closely tracking the changes in various environmental conditions. These conditions include temperature, humidity, wind speed, vapor pressure, vapor pressure deficit, solar intensity and UV intensity.

Treatments were conducted every two hours from 8 pm (20:00) on one day until 10 pm (22:00) the following day. Each treatment was replicated three times, with 12 ears per treatment. The replicates were carried out in different rows to eliminate noise from field variations. Silks were selected prior to pollination to ensure that plants were at a similar point in development. The plants for this experiment had been detasseled so no covering of silks before and after pollination was required.

For each treatment, two forms of controls were used. Three ears per treatment per replication were negative controls and received no pollen. Three ears per treatment per replication were controls receiving pure pollen formulations. The remaining ears in each treatment received a pollen/lactose formulation.

Pure pollen was collected prior to the start of the experiment. A portion of this pollen was stored in a sealed container in pure form at 3 ° C. for use as the pure pollen 24-hour control. Another portion of pollen was similarly stored but used as a 48-hour control. As shown in FIG. 1, the 24-hour old pure pollen performs better than the 48-hour old pure pollen. A portion of freshly collected pollen was mixed into a formulation ratio of one part pollen to five parts powdered lactose. The formulated pollen was stored at 3° C. in a sealed container for 72 hours prior to pollination.

At each time point, 1.5 mL of pollen in formulation was evenly applied to the silks of each plant. For the pure pollen controls, 1.0 mL of pure pollen was evenly applied to the silks of each plant. For negative controls, no pollen was applied.

Results of the experiment are shown in FIG. 1. The chart reports kernel output as a function of time. It is important to note that throughout the experiment, the pollen source is aging, meaning the kernel output would be expected to steadily decline over time. As seen in FIG. 1, the 72-hour old pollen blended with lactose outperforms 48-hour old fresh pollen over various time points. In addition, there is a distinct peak in performance starting at approximately 14:00 on May 29 and continuing until approximately 00:16 on May 30. This timeframe is well outside standard pollination windows.

The experimental results confirm that the performance of pure pollen and pollen mixed with lactose (PP) increases as temperature, vapor pressure deficit, and relative humidity change.

EXAMPLE 2

A series of eleven experiments similar to the experiment outlined in Example 1 were conducted during 2019 and 2020 on corn plants in various locations, including Iowa, Texas and Puerto Rico. The experiments were conducted over different periods of time and at different times of the year, but in all cases, environmental variables were measured throughout the duration of the experiment. These variables included the following: temperature, humidity, wind speed, wind gust speed, dew point, wind chill, wind direction, and barometric readings. In addition, precipitation was observed. Vapor pressure deficit was calculated across the timeframe of the experiments. Either fresh or preserved pollen, or both, were applied at different time points to target maize plants throughout a set time period, and the kernel counts from the resulting ears of corn were obtained. The experimental protocols were essentially as described in Example 1.

These experiments were conducted to demonstrate the factors impacting the timing of intentional pollinations and the resulting success of the pollinations, such as temperature, relative humidity, and vapor pressure deficit. This example is designed to show the efficacy of the method by combining the results of multiple similar experiments to produce charts showing normalized kernel counts in comparison with environmental parameters. Plots of normalized kernel counts vs environmental factors demonstrate that there are ranges for temperature, relative humidity, and VPD during which the success of pollination is improved, enhanced, and/or maximized. To directly compare experiments, the kernel count of each experiment has been normalized to the mean for that experiment. Thus, the kernel counts for each experiment show how the kernel counts increased during selected windows of time to levels exceeding the average number of kernels for that particular experiment.

The experiments were all conducted in female-only blocks. No male plants were present in the blocks of test plants. As a result, the level of natural, unintentional pollination, used as a negative control, was extremely low. Any pollination that occurred would be a result of either insect or wind activity bringing pollen from a physically distant male plant. The negative control ears had approximately 5 kernels per ear, in comparison to the treated ears in the experiments, which had an average of 100 or more kernels per ear. As such, no time-of-day trend was observed in the negative controls because natural pollinations were very low.

In particular, the data demonstrate that the selected window of time for improving or maximizing the success of intentional pollinations falls outside of the time range in which natural pollination occurs, which is typically mid- to late morning. Furthermore, the data demonstrate that by taking advantage of the selected window of time, seed set in the corn plants of the experiment shows a threefold increase over the average kernel count.

Figure 2:
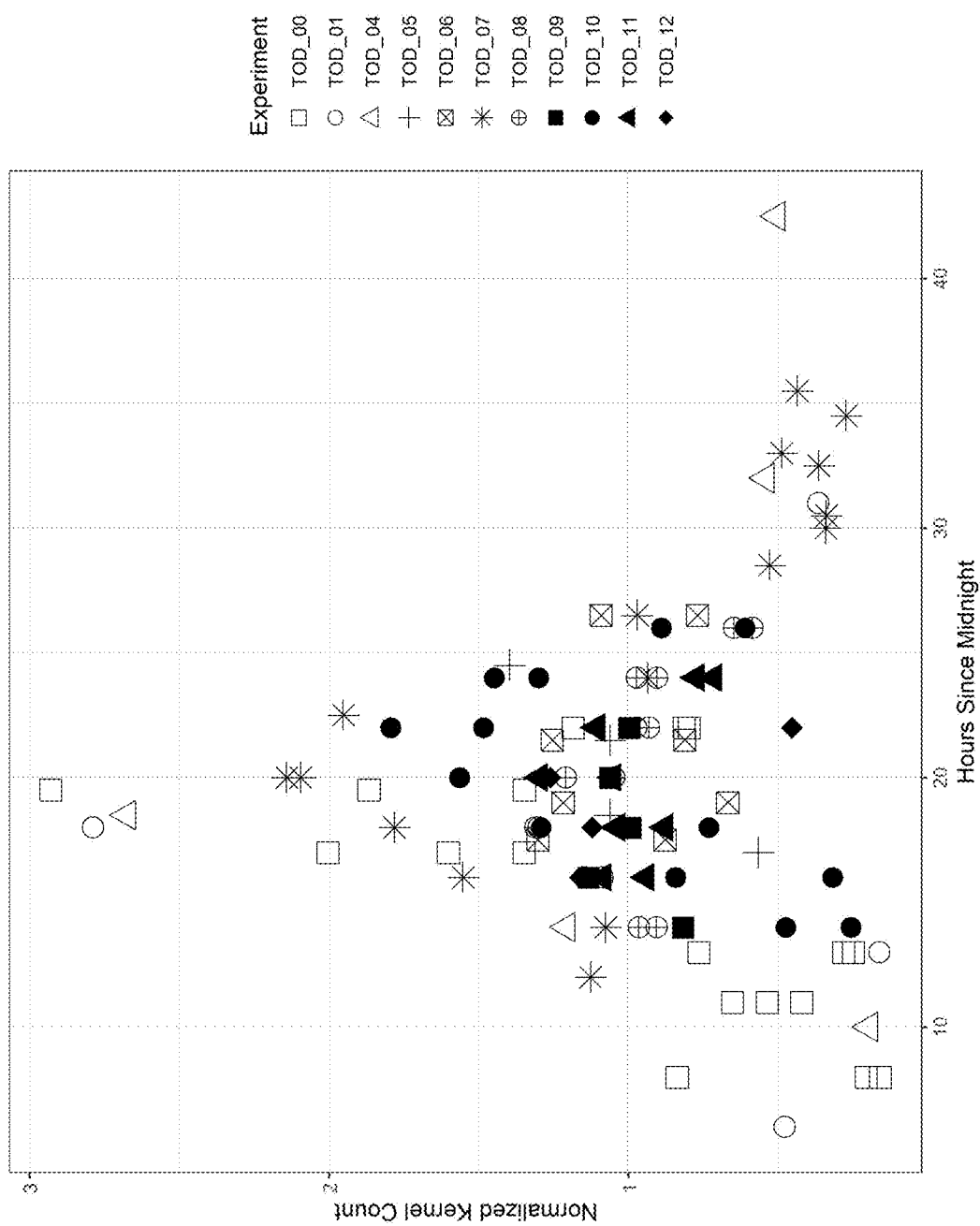
FIG. 2 shows the cumulative results of a series of experiments, with normalized kernel count on the y axis, plotted against the number of hours that have elapsed since midnight on the first day of testing

FIG. 2 shows the normalized kernel count on the y axis, plotted against the number of hours that have elapsed since midnight, thereby showing the hours of the day or days during which the experiments took place. Some experiments were single day, or 24-hour experiments, whereas others were 2-day or 48-hour experiments. FIG. 2 shows the distinct increase in kernel counts during the selected window of time beginning approximately 14 hours after midnight of the previous night, and ending at approximately 24 hours after midnight of the previous night.

Figure 3:
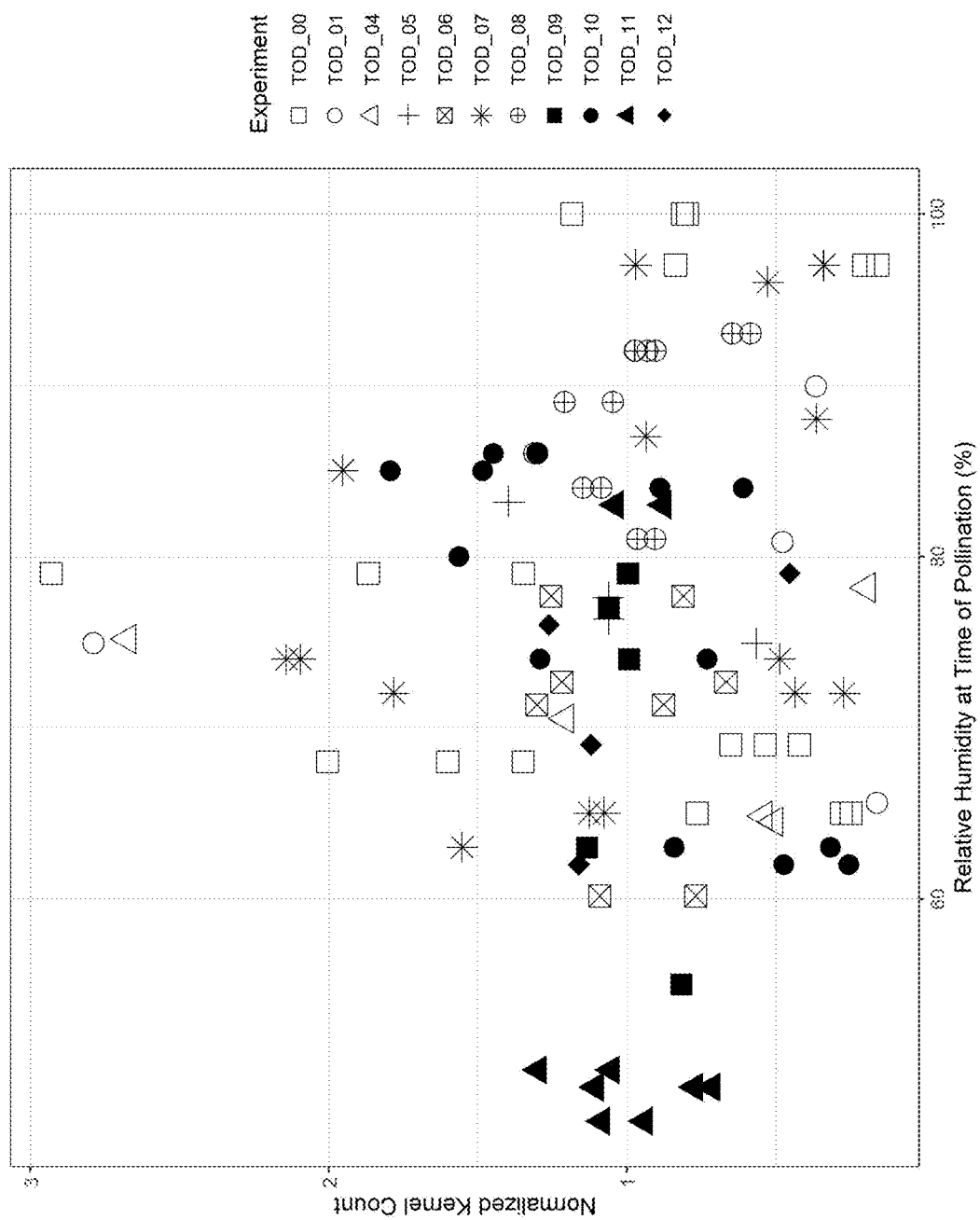
FIG. 3 shows the cumulative results of a series of experiments, with normalized kernel count on the y axis, plotted against the relative humidity percentage at the time of pollination.
Figure 4:
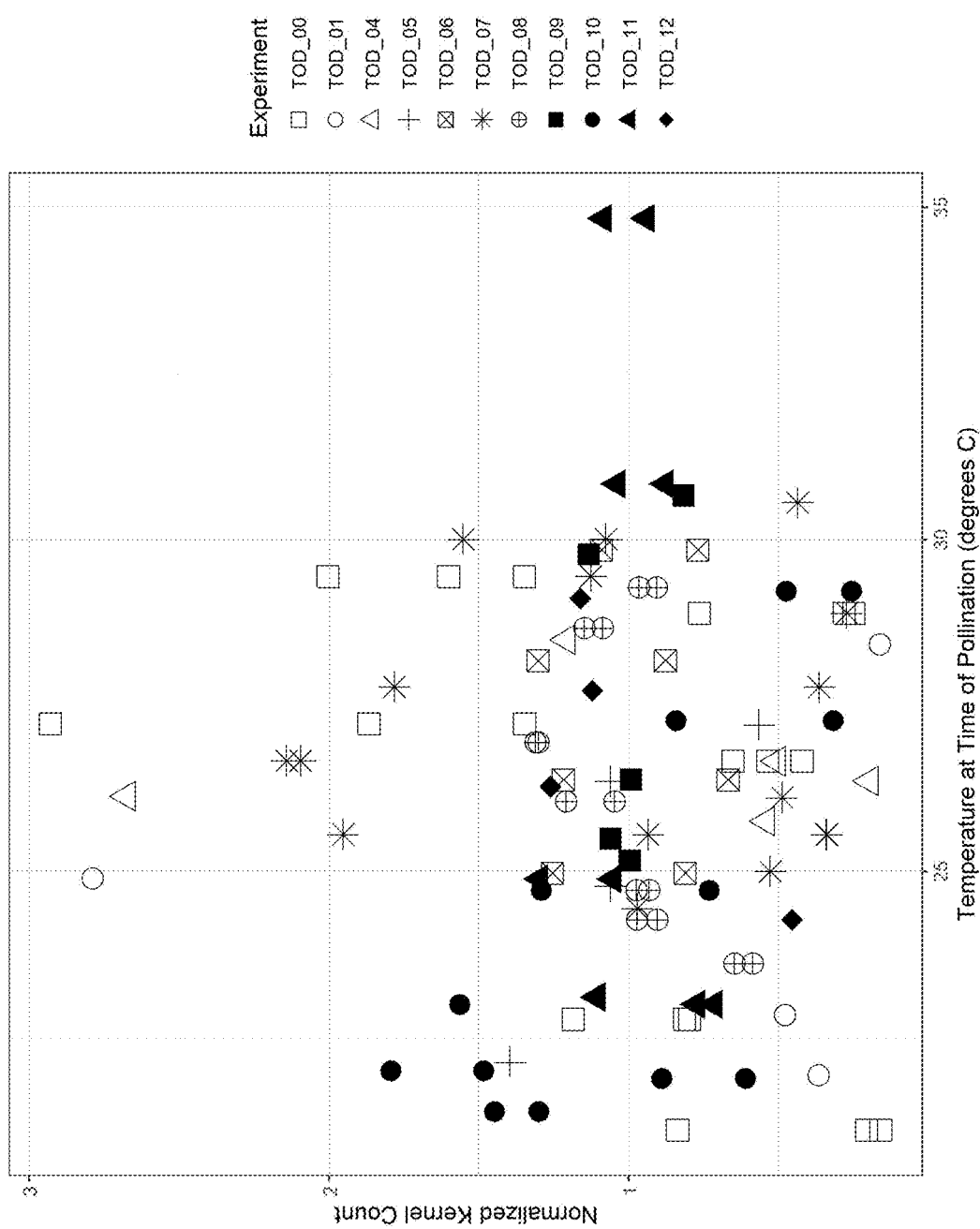
FIG. 4 shows the cumulative results of a series of experiments, with normalized kernel count on the y axis, plotted against the temperature at the time of pollination in degrees Celsius.
Figure 5:
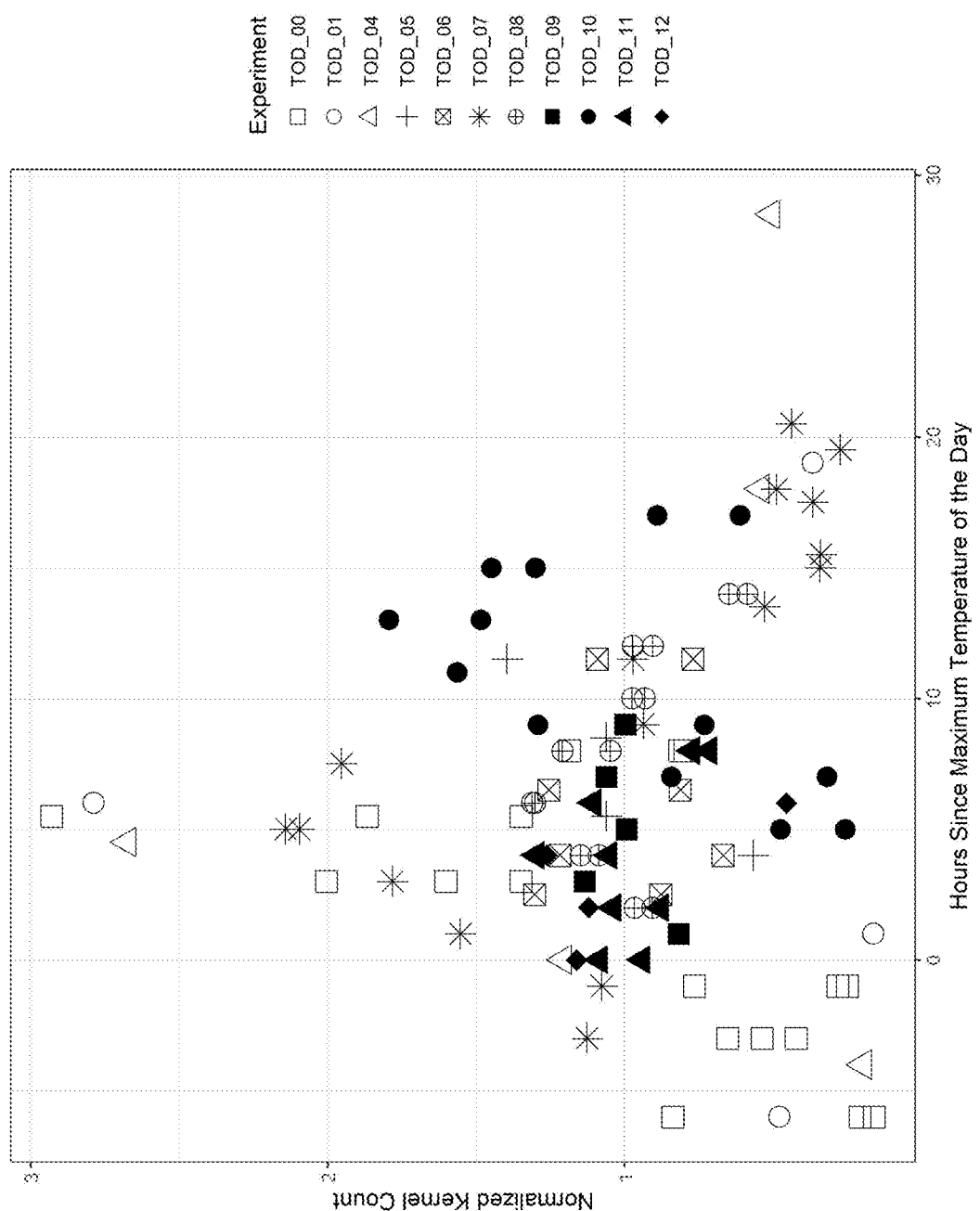
FIG. 5 shows the cumulative results of a series of experiments, with normalized kernel count on the y axis, plotted against the number of hours since the maximum temperature of the day of the experiment.
Figure 6:
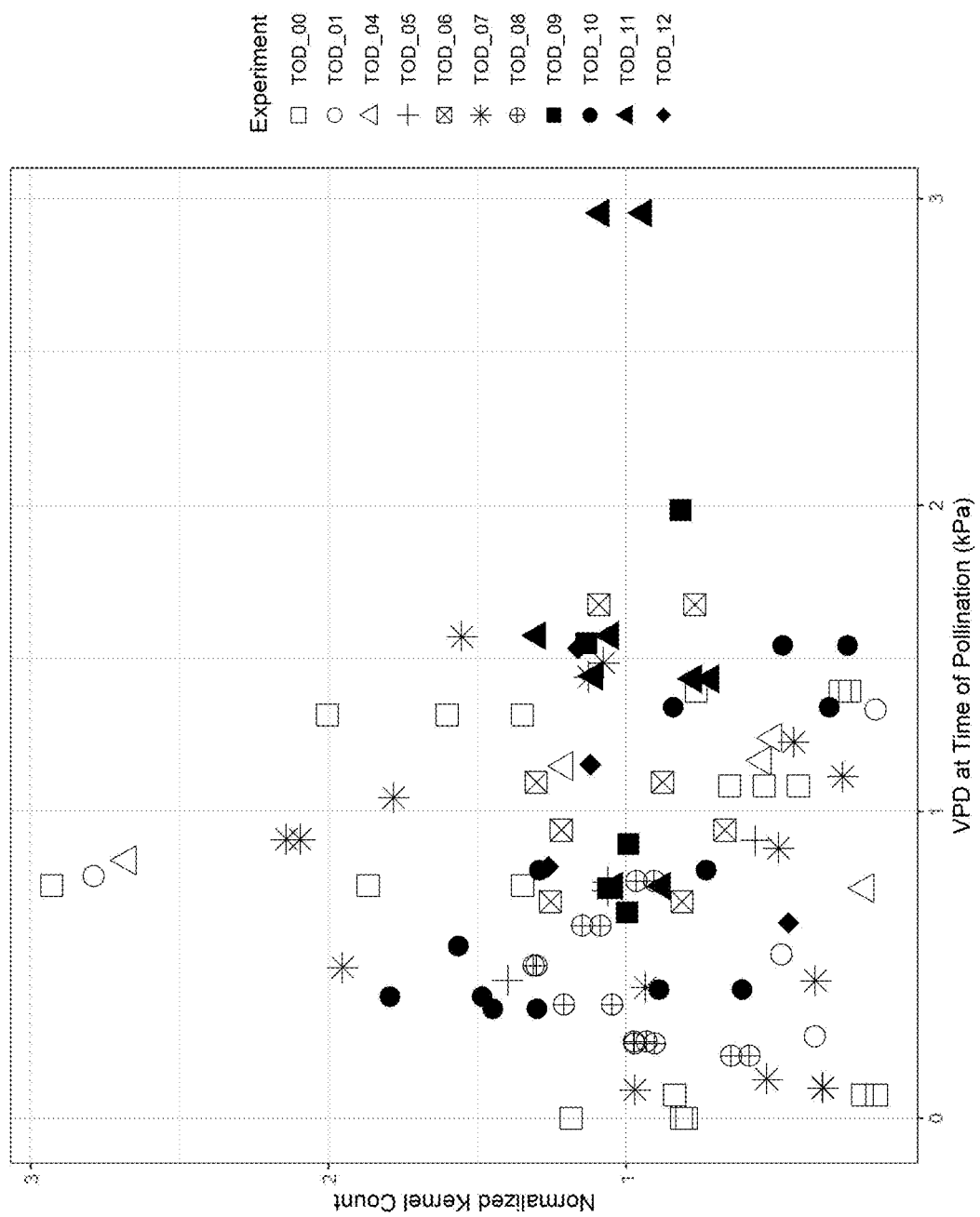
FIG. 6 shows the cumulative results of a series of experiments, with normalized kernel count on the y axis, plotted against the VPD at the time of pollination.

FIG. 3 shows the normalized kernel count on the y axis, plotted against the relative humidity percentage at the time of pollination. FIG. 4 shows the normalized kernel count on the y axis, plotted against the temperature at the time of pollination in degrees Celsius. FIG. 5 shows the normalized kernel count on the y axis, plotted against the number of hours since the maximum temperature of the day. FIG. 6 shows the normalized kernel count on the y axis, plotted against the VPD at the time of pollination. FIGS. 3 through 6 jointly demonstrate that for nine of eleven experiments, the maximum kernel set was achieved approximately four hours after the temperature maximum, relative humidity minimum, and vapor pressure deficit maximum. These three events typically occur within one hour of each other on a typical day. Time of day, temperature, relative humidity and vapor pressure deficit are all demonstrated to be good predictors of the ideal window of time for intentionally applying pollen in order to enhance or maximize seed set (kernel count) or grain yield.

Accordingly, the present invention provides subject matter as defined by the following numbered sub-paragraphs:

1. A method of identifying and/or selecting a selected pollination window in a Poaceae crop comprising:
   (i) monitoring changes in one or more parameters, during a daily monitoring period of multiple hours (for example, at least 2, 3, 4, 5, 6, 7, 8, 9, 10, 11 or more hours), typically wherein said daily monitoring period includes multiple hours between noon (12:00 p.m.). and 11:59 p.m. of the same day, and wherein the step of monitoring the changes optionally includes monitoring changes in one or more parameters during a daily monitoring period on multiple days, wherein said one or more parameters include at least one, and optionally all of, of temperature, and/or vapor pressure deficit, and/or relative humidity; and
   (ii) identifying and/or selecting a selected pollination window for intentionally pollinating said crop, wherein said selected pollination window begins when at least one of the following periods of time has been reached:
      a. when the temperature has been lower than a previous reading of the monitored temperature taken during the daily monitoring period, for at least thirty minutes, optionally wherein the previous reading of the monitored temperature taken during the daily monitoring period is the maximum temperature of the day; and/or b. when the vapor pressure deficit has been lower than a previous reading of the monitored vapor pressure deficit taken during the daily monitoring period, for at least thirty minutes, optionally wherein the previous reading of the monitored vapor pressure deficit taken during the daily monitoring period is the maximum vapor pressure deficit of the day; and/or c. when the relative humidity has been higher than a previously monitored relative humidity taken during the daily monitoring period, for at least thirty minutes, optionally wherein the previous reading of the monitored relative humidity is the minimum relative humidity of the day.

2. The method of sub-paragraph 1 wherein said selected pollination window begins when at least one of the following periods of time has been reached:
   (i) when the temperature has been lower than a previous reading of the monitored temperature taken during the daily monitoring period, for at least one hour; and/or
   (ii) when the vapor pressure deficit has been lower than a previous reading of the monitored vapor pressure deficit taken during the daily monitoring period, for at least one hour; and/or
   (iii) when the relative humidity has been higher than a previous reading of the monitored relative humidity taken during the daily monitoring period for at least one hour.

3. A method of identifying and/or selecting a selected pollination window in a Poaceae crop according to either of sub-paragraph 1 or 2, wherein
   said selected pollination window begins when at least one of the following periods of time has been reached:
   a. a time between when the temperature has been lower than a previously reading of the monitored temperature taken during the daily monitoring period, for at least thirty minutes and 11:59 p.m. of the same day; and/or
   b. a time between when the vapor pressure deficit has been lower than a previous reading of the monitored vapor pressure deficit taken during the daily monitoring period, for at least thirty minutes and 11:59 p.m. of the same day; and/or
   c. a time between when the relative humidity has been higher than a previous reading of the monitored relative humidity taken during the daily monitoring period, for at least thirty minutes and 11:59 p.m. of the same day.

4. A method of enhancing and/or maximizing at least one desirable characteristic of a Poaceae crop comprising intentionally pollinating said crop during a selected pollination window, wherein the selected pollination window is:
(i) identified and/or selected in accordance with the method of any of sub-paragraphs 1, 2 or 3 and wherein at least one of the one or more parameters is temperature, and optionally wherein the previous reading of the monitored temperature taken during the daily monitoring period is the maximum temperature of the day; and/or
   (ii) between 2 hours and 6 hours after the maximum temperature of the day.

5. The method of sub-paragraph 4 wherein said selected pollination window is selected from the group consisting of:
   (iii) 2.5 to 5.5 hours after the maximum recorded temperature of the day,
   (iv) 3 to 5 hours after the maximum recorded temperature of the day,
   (v) 3.5 to 4.5 hours after the maximum recorded temperature of the day.

6. A method of enhancing and/or maximizing at least one desirable characteristic of a Poaceae crop comprising intentionally pollinating said crop during a selected pollination window such that the time at halfway through said intentional pollination is:
   (i) a time that falls within a selected pollination window that has been identified and/or selected in accordance with the method of any of sub-paragraphs 1, 2 or 3, and wherein at least one of the one or more parameters is temperature, and optionally wherein the previous reading of the monitored temperature taken during the daily monitoring period is the maximum temperature of the day; and/or
   (ii) between 2 and 6 hours after the maximum recorded temperature of the day.

7. The method of sub-paragraph 6 wherein the time at halfway through said intentional pollination is selected form the group consisting of:
   (i) 2.5 to 5.5 hours after the maximum recorded temperature of the day,
   (ii) 3 to 5 hours after the maximum recorded temperature of the day,
   (iii) 3.5 to 4.5 hours after the maximum recorded temperature of the day.

8. A method of enhancing and/or maximizing at least one desirable characteristic of a Poaceae crop comprising intentionally pollinating said crop during a selected pollination window, wherein the selected pollination window is:
   (i) identified and/or selected in accordance with the method of any of sub-paragraphs 1, 2 or 3 and wherein at least one of the one or more parameters is vapor pressure deficit, and optionally wherein the previous reading of the monitored vapor pressure deficit taken during the daily monitoring period is the maximum vapor pressure deficit of the day; and/or
   (ii) between 2 and 6 hours after the maximum recorded vapor pressure deficit of the day.

9. The method of sub-paragraph 8 wherein said selected pollination window is selected from the group consisting of:
   (i) 2.5 to 5.5 hours after the maximum recorded vapor pressure deficit of the day,
   (ii) 3 to 5 hours after the maximum recorded vapor pressure deficit of the day,
   (iii) 3.5 to 4.5 hours after the maximum recorded vapor pressure deficit of the day.

10. A method of enhancing and/or maximizing at least one desirable characteristic of a Poaceae crop comprising intentionally pollinating said crop during a selected pollination window such that the time at halfway through said intentional pollination is:
    (i) a time that falls within a selected pollination window that has been identified and/or selected in accordance with the method of any of sub-paragraphs 1, 2 or 3, and wherein at least one of the one or more parameters is vapor pressure deficit, and optionally wherein the previous reading of the monitored vapor pressure deficit taken during the daily monitoring period is the maximum vapor pressure deficit of the day ; and/or
(ii) between 2 and 6 hours after the maximum recorded vapor pressure deficit of the day.

11. The method of sub-paragraph 10 wherein the time at halfway through said intentional pollination is selected form the group consisting of:
   (i) 2.5 to 5.5 hours after the maximum recorded vapor pressure deficit of the day,
   (ii) 3 to 5hours after the maximum recorded vapor pressure deficit of the day,
   (iii) 3.5 to 4.5 hours after the maximum recorded vapor pressure deficit of the day.

12. A method of maximizing at least one desirable characteristic of a Poaceae crop comprising intentionally pollinating said crop during a selected pollination window that is between 2 hours and 6 hours after the minimum recorded relative humidity of the day.

13. The method of paragraph 8 wherein said selected pollination window is selected from the group consisting of:
   (iv) 2.5 to 5.5 hours after the minimum recorded relative humidity of the day,
   (v) 3 to 5 hours after the minimum recorded relative humidity of the day,
   (vi) 3.5 to 4.5 hours after the minimum recorded relative humidity of the day.

14. A method of maximizing at least one desirable characteristic of a Poaceae crop comprising intentionally pollinating said crop during a selected pollination window such that the time at halfway through said intentional pollination is between 2 and 6 hours after the minimum recorded relative humidity of the day.

15. The method of paragraph 10 wherein the time at halfway through said intentional pollination is selected form the group consisting of:
   (iv) 2.5 to 5.5 hours after the minimum recorded relative humidity of the day,
   (v) 3 to 5 hours after the minimum recorded relative humidity of the day,
   (vi) 3.5 to 4.5 hours after the minimum recorded relative humidity of the day.

16. A method of identifying a Poaceae crop as being ready for intentional pollination during a selected pollination window, wherein the step of selecting and/or identifying said crop as being ready for intentional pollination comprises:
   (i) Monitoring one or more parameters, during a daily monitoring period of multiple hours (for example, at least 2, 3, 4, 5, 6, 7, 8, 9, 10, 11 or more hours), typically wherein said daily monitoring period includes multiple hours between noon (12:00 p.m.) and 11:59 p.m. of the same day, wherein said one more parameters include the temperature to which said crop is exposed, and optionally wherein the step of monitoring the one or more parameters includes monitoring the one or more parameters during a daily monitoring period on multiple days, and
   (ii) Selecting and/or identifying said crop as being ready for intentional pollination during said selected pollination window, if said crop is determined to be at one of the following periods of time:
      a. a time that falls within a selected pollination window that has been identified and/or selected in accordance with the method of any of sub-paragraphs 1, 2 or 3, and wherein at least one of the one or more parameters is temperature, and optionally wherein the previous reading of the monitored temperature taken during the daily monitoring period is the maximum measured temperature of the day,
      b. 2 to 6 hours after the maximum measured temperature,
      c. 2.5 to 5.5 hours after the maximum measured temperature,
      d. 3 to 5 hours after the maximum measured temperature, and/or
      e. 3.5 to 4.5 hours after the maximum measured temperature.

17. A method of selecting and/or identifying a Poaceae crop as being ready for intentional pollination during a selected pollination window, wherein the step of selecting and/or identifying said crop as being ready for intentional pollination comprises:
   (iii) Monitoring one or more parameters, during a daily monitoring period of multiple hours (for example, at least 2, 3, 4, 5, 6, 7, 8, 9, 10, 11 or more hours), typically wherein said daily monitoring period includes multiple hours between noon (12:00 p.m.) and 11:59 p.m. of the same day, wherein said one or more parameters include the vapor pressure deficit to which said crop is exposed, optionally wherein the step of monitoring the one or more parameters includes monitoring the one or more parameters during a daily monitoring period on multiple days, and
   (iv) Selecting and/or identifying said crop as being ready for intentional pollination during said selected pollination window, if said crop is determined to be at one of the following periods of time:
      a. a time that falls within a selected pollination window that has been identified and/or selected in accordance with the method of any of sub-paragraphs 1, 2 or 3, and wherein at least one of the one or more parameters is vapor pressure deficit, and optionally wherein the previous reading of the monitored vapor pressure deficit taken during the daily monitoring period is the maximum measured vapor pressure deficit of the day,
      b. 2 to 6 hours after the maximum measured vapor pressure deficit,
      c. 2.5 to 5.5 hours after the maximum measured vapor pressure deficit,
      d. 3 to 5 hours after the maximum measured vapor pressure deficit, and/or
      e. 3.5 to 4.5 hours after the maximum measured vapor pressure deficit.

18. A method of identifying a Poaceae crop as being ready for intentional pollination during a selected pollination window, wherein the step of identifying said crop as being ready for intentional pollination comprises:
   (v) Monitoring one or more parameters from 12:00 p.m. to 11:59 p.m., wherein said parameters include the relative humidity to which said crop is exposed, and
   (vi) Identifying said crop as being ready for intentional pollination during said selected pollination window, if said crop is presented for intentional pollination at one of the following periods of time:
      a. 2 to 6 hours after the minimum recorded humidity, b. 2.5 to 5.5 hours after the minimum recorded relative humidity,
c. 3 to 5 hours after the minimum recorded relative humidity, and/or
d. 3.5 to 4.5 hours after the minimum recorded relative humidity.
19. The method of any preceding sub-paragraph further comprising the step of intentionally releasing pollen one or more times during the selected pollination window.
20. The method of sub-paragraph 19, wherein the step of intentionally releasing pollen comprises releasing the pollen in proximity to said crop.
21. The method of sub-paragraph 19 wherein said pollen that is intentionally released is selected from the group consisting of fresh pollen, preserved pollen, and combinations thereof.
22. The method of sub-paragraph 19 wherein said pollen that is intentionally released is preserved pollen which has been harvested from one or more of a field, a growth chamber, a greenhouse, a glasshouse, a shade house, a hoop house, a vertical farming facility, or a hydroponic facility.
23. The method of sub-paragraph 19 wherein said pollen that is intentionally released is preserved pollen that has been previously collected and preserved by cooling, chilling, cryopreservation, freezing, freeze drying, storage with additives that improve pollen longevity, or storage in liquid nitrogen.
24. The method of sub-paragraph 19 wherein said pollen that is intentionally released has been collected from one or more of:
  i. a source with altered circadian rhythm; and
  ii. a source with normal circadian flowering, but wherein said male components of said designated female patent plants are delayed.
25. The method of sub-paragraph 19 wherein said pollen that is intentionally released is obtained from a single plant source.
26. The method of sub-paragraph 19 wherein said pollen that is intentionally released is obtained from multiple sources and is combined prior to application.
27. The method of any proceeding sub-paragraph, wherein optionally the method is not a method of the production of plants, for example wherein the method comprises growing the intentionally pollinated crop to produce seed, and wherein the seed is, or is destined to be, used as grain, such as seed for use in human food products, animal food products, ethanol production, oil production, or any other seed use in which the seed is not intended for planting and in which the seed is typically destroyed or rendered non-viable.
28. The method of any preceding sub-paragraph, wherein the method comprises growing the intentionally pollinated crop to produce seed, and further comprises using said seed to make food for human consumption, animal feed, fuel including but not limited to ethanol, biomass, and/or other nutritional products.
29. The method of any preceding sub-paragraph wherein said selected pollination window begins between noon (12:00 p.m.) and 11:59 p.m. of the same day.
30. The method of any preceding sub-paragraph wherein an intentional release of pollen begins between noon (12:00 p.m.) and 11:59 p.m. of the same day.
31. The method of any preceding sub-paragraph wherein said selected pollination window occurs when the humidity is at least 75%.
32. The method of any preceding sub-paragraph wherein said selected pollination window occurs when the humidity is 75% to 90%.
33. The method of any preceding sub-paragraph wherein said selected pollination window occurs on a day when at least a portion of the crop is receptive to pollen, for example wherein the crop is a population of Poaceae plants, at least 10%, 20%, 30%, 40%, 50%, 60%, 70%, 80%, 90%, 95% or more, such as substantially 100% of the Poaceae plants in the population are receptive to pollen.
34. The method of sub-paragraph 28 wherein said crop is receptive to pollen.
35. The method of any of the preceding sub-paragraphs wherein said method maximizes and/or enhances seed set, yield, and/or content of oil, starch, protein, and/or other nutritional components.
36. The method of any of the preceding sub-paragraphs wherein said method is practiced on a population of Poaceae plants.
37. The method of any of the preceding sub-paragraphs wherein pollination occurs between 4:00 p.m. and 6:00 p.m.
38. The method of any of the preceding sub-paragraphs wherein the method does not include a step of intentionally releasing pollen.
39. The method of any of the preceding sub-paragraphs wherein the method is not an essentially biological process for the production of plants.
40. The method of any of the preceding sub-paragraphs wherein the method does not comprise:
  (i) the step of selecting any one or more progeny that results from the pollination of the crop,
  (ii) the production of seeds by the crop resulting from said pollination,
  (iii) the germination of one or more of those seeds to generate one or more progeny,
  (iv) the selection of a plant variety,
  (v) the generation of a plant variety, and/or
  (vi) the collection of any seed produced by the crop.
41. The method of any of the preceding sub-paragraphs wherein said selected pollination window is identified and/or selected by a method that is one or more of an automated method and a computer-implemented method.
42. An apparatus for selecting identifying a selected pollination window in a Poaceae crop, the apparatus comprising one or more processors and memory, in which the memory comprises computer program code configured to cause a processor to:
  a. monitor changes in one or more parameters, during a daily monitoring period of multiple hours (for example, at least 2, 3, 4, 5, 6, 7, 8, 9, 10, 11 or more hours), typically wherein said daily monitoring period includes multiple hours between noon (12 p.m.) and 11:59 p.m. of the same day, and wherein the monitored changes optionally includes monitored changes in one or more parameters during a daily monitoring period on multiple days, wherein said one or more parameters include at least one, and optionally all of, of temperature and/or vapor pressure deficit and/or relative humidity; and
  b. identify and/or select a selected pollination window for intentionally pollinating said crop, wherein said selected pollination window begins when at least one of the following periods of time has been reached:

(i) when the temperature has been lower than a previous reading of the monitored temperature taken during the daily monitoring period, for at least thirty minutes, optionally wherein the previous reading of the monitored temperature taken during the daily monitoring period is the maximum temperature of the day; and/or (ii) when the vapor pressure deficit has been lower than a previous reading of the monitored vapor pressure deficit taken during the daily monitoring period, for at least thirty minutes, optionally wherein the previous reading of the monitored vapor pressure deficit taken during the daily monitoring period is the maximum vapor pressure deficit of the day; and/or (iii) when the relative humidity has been higher than a previous reading of the monitored relative humidity taken during the daily monitoring period, for at least thirty minutes, optionally wherein the previous reading of the monitored relative humidity taken during the daily monitoring period is the minimum relative humidity of the day.

43. An apparatus for selecting a selected pollination window in a Poaceae crop, optionally according to sub-paragraph 38, wherein the apparatus comprises one or more processors and memory, in which the memory comprises computer program code configured to cause a processor to:

(i) monitor changes in one or more parameters from about noon (12:00 p.m.). to about 11:59 p.m. of the same day, on one or more days, wherein said one or more parameters include at least one of temperature, and/o, vapor pressure deficit, and/or relative humidity; and (ii) identify and/or select a selected pollination window for intentionally pollinating said crop, wherein said selected pollination window begins when at least one of the following periods of time has been reached:
   a. when the temperature has been lower than a previously monitored temperature for at least thirty minutes;
   b. when the vapor pressure deficit has been lower than a previously monitored vapor pressure deficit for at least thirty minutes;
   c. when the relative humidity has been higher than a previously monitored relative humidity for at least thirty minutes.

44. The apparatus of sub-paragraph 42 or 43 wherein said apparatus is selected from one or more of an on-site computer, remote server, and cell phone.

45. The apparatus of any of sub-paragraphs 42 to 44, in which monitoring changes in the one or more parameters comprises receiving the one or more parameters from remote data logging hardware, wherein the remote data logging hardware is optionally at the site of the Poaceae crop.

46. The apparatus of any of sub-paragraphs 42 to 44, in which monitoring changes in the one or more parameters comprises receiving the one or more parameters from a user input device.

47. The apparatus of sub-paragraph 46 wherein the user input device is remote from said apparatus.

48. The apparatus of sub-paragraph 46 wherein the user input device communicates with said apparatus over a computer network.

49. The apparatus of any of sub-paragraphs 42 to 48, further comprising a thermometer configured to monitor at least one of the temperature of the crop and the air temperature at said crop.

50. The apparatus of any of sub-paragraphs 42 to 49, further comprising at least one means for measuring vapor pressure deficit.

51. The apparatus of sub-paragraph 45 wherein said at least one means for measuring vapor pressure deficit is configured to monitor the vapor pressure deficit at said crop.

52. The apparatus of any of sub-paragraphs 42 to 51, further comprising at least one means for measuring relative humidity.

53. The apparatus of sub-paragraph 52 wherein said at least one means for measuring relative humidity is configured to monitor the vapor pressure deficit at said crop.

54. The apparatus of any of sub-paragraphs 42 to 53, further configured to provide, for example via a computer network, the selected pollination window to a remote user for assisting the user in determining the time for performing a step of intentional release of pollen, and/or for performing a step of intentional pollination of the crop.

55. The apparatus of any of sub-paragraphs 42 to 54, further comprising an output device for providing an indication of the selected pollination window to a user for assisting the user in determining the time for performing a step of intentional release of pollen, and/or for performing a step of intentional pollination of the crop.

56. The apparatus of sub-paragraph 55, wherein the output device may be a display device, an audio output device, or a device for providing haptic feedback, for example.

57. The apparatus of any of sub-paragraphs 42 to 55, further configured to activate Poaceae crop pollination equipment based on the selected pollination window.

58. Computer program code for selecting a selected pollination window in a Poaceae crop, the computer program code configured to cause a processor to:
   a. monitor changes in one or more parameters, during a daily monitoring period of multiple hours (for example, at least 2, 3, 4, 5, 6, 7, 8, 9, 10, 11 or more hours), typically wherein said daily monitoring period includes multiple hours between noon (12 p.m.) and 11:59 p.m. of the same day, and wherein the monitored changes optionally includes monitored changes in one or more parameters during a daily monitoring period on multiple days, wherein said one or more parameters include at least one, and optionally both, of temperature, and/or vapor pressure deficit, and/or relative humidity; and
   b. identify and/or select a selected pollination window for intentionally pollinating said crop, wherein said selected pollination window begins when at least one of the following periods of time has been reached:
      (i) when the temperature has been lower than a previous reading of the monitored temperature taken during the daily monitoring period, for at least thirty minutes, optionally wherein the previous reading of the monitored temperature taken during the daily monitoring period is the maximum temperature of the day; and/or
      (ii) when the vapor pressure deficit has been lower than a previous reading of the monitored vapor pressure deficit taken during the daily monitoring period, for at least thirty minutes, optionally wherein the previous reading of the monitored vapor pressure deficit taken during the daily monitoring period is the maximum vapor pressure deficit of the day; and/or (iii) when the relative humidity has been higher than a previous reading of the monitored relative humidity taken during the daily monitoring period, for at least thirty minutes, optionally wherein the previous reading of the monitored relative humidity taken during the daily monitoring period is the minimum relative humidity of the day.

59. Computer program code, optionally according to sub-paragraph 58, for selecting and/or identifying a selected pollination window in a Poaceae crop, the computer program code configured to cause a processor to:
   (i) monitor changes in one or more parameters from noon (12:00 p.m.). to 11:59 p.m of the same day, on one or more days, wherein said one or more parameters include at least one of temperature, and/or vapor pressure deficit, and/or relative humidity; and
   (ii) identify and/or select a selected pollination window for intentionally pollinating said crop, wherein said selected pollination window begins when at least one of the following periods of time has been reached:
      a. when the temperature has been lower than a previously monitored temperature for at least thirty minutes;
      d. when the vapor pressure deficit has been lower than a previously monitored vapor pressure deficit for at least thirty minutes;
      b. when the relative humidity has been higher than a previously monitored relative humidity for at least thirty minutes.

60. An apparatus for identifying a pollination window for a Poaceae crop, the apparatus comprising one or more processors and memory, in which the memory comprises computer program code configured to cause a processor to:
   (i) monitor changes in one or more parameters over time, wherein said one or more parameters include the temperature, and/or vapor pressure deficit, and/or relative humidity to which the Poaceae crop is exposed,
   (ii) identifying the pollination window for the Poaceae crop based on the one or more parameters.

61. The apparatus of sub-paragraph 60 wherein the selected pollination window is selected from those provided in sub-paragraphs 1, 10-25, 28, and/or 33.

62. Any of the preceding sub-paragraphs wherein the crop is selected from the group consisting of maize, wheat, rice, sorghum, barley, oats, and pearl millet.

63. Any of the preceding sub-paragraphs wherein measuring said parameters includes one or more of measuring and/or recording said parameters.

64. The method of any preceding sub-paragraph wherein monitoring is continuous or is measured at multiple intervals, for example, intervals of every 1 second, 5 seconds, 10 seconds, 15 seconds, 20 seconds, 25 seconds, 30 seconds, 35 seconds, 40 seconds, 45 seconds, 50 seconds, 55 seconds, 60 seconds, 75 seconds, 90 seconds, 105 seconds, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 20 minutes, 25 minutes, 30 minutes, 45 minutes, or 60 minutes.

Although various representative embodiments of this invention have been described above with a certain degree of particularity, those skilled in the art could make numerous alterations to the disclosed embodiments without departing from the spirit or scope of the inventive subject matter set forth in the specification and claims. In some instances, in methodologies directly or indirectly set forth herein, various steps and operations are described in one possible order of operation, but those skilled in the art will recognize that steps and operations may be rearranged, replaced, or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

Although the present invention has been described with reference to the embodiments outlined above, various alternatives, modifications, variations, improvements and/or substantial equivalents, whether known or that are or may be presently foreseen, may become apparent to those having at least ordinary skill in the art. Listing the steps of a method in a certain order does not constitute any limitation on the order of the steps of the method. Accordingly, the embodiments of the invention set forth above are intended to be illustrative, not limiting. Persons skilled in the art will recognize that changes may be made in form and detail without departing from the spirit and scope of the invention. Therefore, the invention is intended to embrace all known or earlier developed alternatives, modifications, variations, improvements, and/or substantial equivalents. Furthermore, unless specifically indicated to the contrary, reference to a time range, window, and/or period may be "approximate" or "about", such as being plus or minutes 1, 2, 3, 4, 5, 10, 15, 20, 25, or 30 minutes.

The invention claimed is:

1. A method of intentionally pollinating a Poaceae crop comprising:
   (i) monitoring changes in one or more parameters for a period of time between 12:00 p.m. to 11:59 p.m. on one or more days, wherein said one or more parameters are selected from the group consisting of temperature, vapor pressure deficit, and relative humidity; and
   (ii) intentionally pollinating said crop with collected and stored pollen, wherein said pollination begins after at least one of the following periods of time has been reached:
      a. when the temperature is between 7 and 38 degrees Celsius and has been lower than a previously monitored temperature for at least thirty minutes, before 11:59 pm on the same day;
      b. when the vapor pressure deficit is between 0.1 and 1.5 kPa and has been lower than a previously monitored vapor pressure deficit for at least thirty minutes, before 11:59 pm on the same day;
      c. when the relative humidity is between 75% and 98% and has been higher than a previously monitored relative humidity for at least thirty minutes, before 11:59 pm on the same day;
   wherein said intentional pollination results in one or more outcomes selected from the group consisting of maximizing yield, maximizing seed set, or maximizing a desirable characteristic of the crop.

2. The method of claim 1 wherein said intentional pollination begins when at least one of the following periods of time has been reached:
  (i) when the temperature is between 7 and 38 degrees Celsius and has been lower than a previously monitored temperature on the same day for a period of time ranging from at least 45 minutes to at least 90 minutes;
  (ii) when the vapor pressure deficit is between 0.1 and 1.5 kPa and has been lower than a previously monitored vapor pressure deficit on the same day for a period of time ranging from at least 45 minutes to at least 90 minutes; and
  (iii) when the relative humidity is between 75% and 98% and has been higher than a previously monitored relative humidity on the same day for a period of time ranging from at least 45 minutes to at least 90 minutes.

3. The method of claim 1 wherein said pollen is from the group consisting of freshly collected and stored pollen, previously collected and preserved pollen, and combinations thereof.

4. The method of claim 1 wherein said pollen has previously been collected from one or more of a field, a growth chamber, a greenhouse, a glasshouse, a shade house, a hoop house, a vertical farming facility, or a hydroponic facility.

5. The method of claim 3 wherein said pollen is preserved pollen that has been preserved by cooling, chilling, cryopreservation, freezing, freeze drying, storage with additives that improve pollen longevity, or storage in liquid nitrogen.

6. The method of claim 3 wherein said pollen has been collected from one or more of:
  (i) a source with altered circadian rhythm; and
  (ii) a source with normal circadian flowering, but wherein male components of female parent plants are delayed.

7. The method of claim 3 wherein said pollen is obtained from a single plant source.

8. The method of claim 3 wherein said pollen is obtained from multiple sources and is combined prior to application.

9. The method of claim 3 wherein pollination occurs between 4:00 p.m. and 6:00 p.m.

10. The method of claim 1 wherein the crop is selected from the group consisting of maize, wheat, rice, sorghum, barley, oats, and pearl millet.

11. The method of claim 1 wherein said monitoring is continuous or occurs at regular intervals ranging from 1 second intervals to 60 minute intervals.

12. The method of claim 1 wherein said intentional pollination occurs between 2 hours and 6 hours after the maximum temperature of the day.

13. The method of claim 12 wherein said pollination occurs at a time selected from the group consisting of:
  (i) 2.5 to 5.5 hours after the maximum recorded temperature of the day,
  (ii) three to five hours after the maximum recorded temperature of the day, and/or
  (iii) 3.5 to 4.5 hours after the maximum recorded temperature of the day.

14. The method of claim 1, wherein said desirable characteristic is selected from the group consisting of starch content, oil content, and protein content.

* * * * *